US010167508B2

(12) United States Patent
Song et al.

(10) Patent No.: US 10,167,508 B2
(45) Date of Patent: Jan. 1, 2019

(54) DETECTION OF GENETIC ABNORMALITIES

(75) Inventors: Ken Song, San Jose, CA (US); Arnold Oliphant, San Jose, CA (US); John Stuelpnagel, San Jose, CA (US); Andrew Sparks, San Jose, CA (US)

(73) Assignee: ARIOSA DIAGNOSTICS, INC., San Jose, CA (US)

( * ) Notice: Subject to any disclaimer, the term of this patent is extended or adjusted under 35 U.S.C. 154(b) by 34 days.

(21) Appl. No.: 13/407,978

(22) Filed: Feb. 29, 2012

(65) Prior Publication Data

US 2012/0164646 A1 Jun. 28, 2012

Related U.S. Application Data

(63) Continuation-in-part of application No. 13/013,732, filed on Jan. 25, 2011, now abandoned, and a continuation-in-part of application No. 13/205,490, filed on Aug. 8, 2011, now abandoned, and a continuation-in-part of application No. 13/205,570, filed on Aug. 8, 2011, now Pat. No. 9,890,421, and a continuation-in-part of application No. 13/205,603, filed on Aug. 8, 2011.

(60) Provisional application No. 61/448,067, filed on Mar. 1, 2011, provisional application No. 61/371,605, filed on Aug. 6, 2010.

(51) Int. Cl.
*C12Q 1/6883* (2018.01)

(52) U.S. Cl.
CPC ..... *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 3/1999 | Zhang et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,141,096 A | 10/2000 | Stern et al. |
| 6,156,504 A | 12/2000 | Gocke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |

(Continued)

FOREIGN PATENT DOCUMENTS

| | | |
|---|---|---|
| GB | 2299166 | 9/1996 |
| GB | 970444 | 3/1997 |

(Continued)

OTHER PUBLICATIONS

Centre for Genetics Education (retrieved on Oct. 8, 2013 from the internet: <http://web.archive.org/web/20080720002551/http://www.genetics.edu.au/pdf/factsheets/fs07.pdf>).*
Shen et al. BMC Genetics. 2008. 9:27.*
Heilig, et al., "The DNA sequence and analysis of human chromosome 14", Nature, 421:601-09 (2003).
Hosny, et al., "TP53 mutations in circulating fee DNA from Egyptian patients with non-Hodgkin's lymphoma", Cancer Lett., 275(2):234-39 (2009).
Irizarry, et al., "Summaries of Affymetrix GeneChip probe level data", Nuc. Acid Res., 31(4):e5 (2003).
Kamnasaran and Cox, "Current status of chromosome 14", J. Med. Genet., 39:81-90 (2002).
Landegren, et al., "A ligase-mediated gene detection technique", Science, 241:1077 (1988).

(Continued)

*Primary Examiner* — Joseph G. Dauner
(74) *Attorney, Agent, or Firm* — Mintz, Levin, Cohn, Ferris, Glovsky and Popeo, P.C.

(57) ABSTRACT

The present invention provides assay systems and related methods for determining genetic abnormalities in mixed samples comprising cell free DNA from both normal and putative genetically atypical cells. Exemplary mixed samples for analysis using the assay systems of the invention include samples comprising both maternal and fetal cell free DNA and samples that contain DNA from normal cells and circulating cancerous cells.

29 Claims, 1 Drawing Sheet

(56) References Cited

U.S. PATENT DOCUMENTS

| | | |
|---|---|---|
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,316,229 B1* | 11/2001 | Lizardi et al. ............... 435/91.1 |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Lo |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian et al. |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,293,076 B2 | 10/2012 | Fan et al. |
| 8,318,430 B2 | 11/2012 | Chuu et al. |
| 2001/0051341 A1* | 12/2001 | Lo ................... C12Q 1/6879 435/6.12 |
| 2002/0045176 A1 | 4/2002 | Lo |
| 2002/0013224 A1* | 9/2002 | Fan .................... 435/6 |
| 2002/0160361 A1* | 10/2002 | Loehrlein ............ C12Q 1/6809 435/6.18 |
| 2003/0044388 A1 | 3/2003 | Lo et al. |
| 2003/0054386 A1 | 3/2003 | Antonarakis et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0203037 A1 | 10/2004 | Lo et al. |
| 2004/0214175 A9 | 10/2004 | McKernan et al. |
| 2005/0095618 A1 | 5/2005 | Tsui et al. |
| 2005/0191656 A1 | 9/2005 | Drmanac et al. |
| 2006/0121452 A1* | 6/2006 | Dhallan .......................... 435/5 |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0090239 A1* | 4/2008 | Shoemaker ........ G01N 33/5091 435/6.12 |
| 2008/0096766 A1 | 4/2008 | Lee |
| 2008/0138809 A1 | 6/2008 | Kapur et al. |
| 2008/0206749 A1 | 8/2008 | Olson et al. |
| 2008/0243398 A1 | 10/2008 | Rabinowitz |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0159499 A1 | 6/2011 | Hindson |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0039724 A1 | 2/2012 | Rossi |
| 2012/0040859 A1 | 2/2012 | Sparks et al. |
| 2012/0100548 A1 | 4/2012 | Rava et al. |
| 2012/0108460 A1 | 5/2012 | Quake et al. |

(56) References Cited

U.S. PATENT DOCUMENTS

| | | |
|---|---|---|
| 2012/0165203 A1 | 6/2012 | Quake et al. |
| 2012/0184449 A1 | 6/2012 | Hixson |
| 2012/0191359 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0225798 A1 | 9/2012 | Cantor et al. |
| 2012/0230258 A1 | 9/2012 | Miki |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |
| 2013/0004950 A1 | 1/2013 | Sparks et al. |
| 2013/0029852 A1 | 1/2013 | Rava |
| 2013/0090250 A1 | 4/2013 | Sparks et al. |

FOREIGN PATENT DOCUMENTS

| | | |
|---|---|---|
| WO | WO87/006270 | 10/1987 |
| WO | WO90/06995 | 6/1990 |
| WO | WO99/47964 | 9/1999 |
| WO | WO2003/038120 | 5/2003 |
| WO | WO2007/100243 | 9/2007 |
| WO | WO2007/126377 | 11/2007 |
| WO | WO2008/118998 | 10/2008 |
| WO | WO2009/102632 | 8/2009 |
| WO | WO2011/090556 | 1/2010 |
| WO | WO2011/090557 | 1/2010 |
| WO | WO2011/090558 | 1/2010 |
| WO | WO-2012/019198 A2 | 2/2012 |
| WO | WO-2012/019198 A3 | 2/2012 |

OTHER PUBLICATIONS

Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", AM J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010).
Lo, "Fetal nucleic acids in maternal blood: the promises", Clin. Chem. Lab Med., 50(5):xxx-xxx (DOI 10.1515/CCLM.2011.765) (2011).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).

Makrigiorgos, et al., "A PCR-based amplification method retaining the quantitative difference between two complex genomes", Nat. Biotech., 20:936-39 (2002).
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", Anzjog, 45(6):529-32 (2005).
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz, et al., "Microsatellite alterations in serum DNA of head and neck cancer patients", Nature Medicine, 2(9):1035-37 (1996).
Ng, et al., "mRNA of placental origin is readily detectable in maternal plasma", PNAS USA, 100:4748-53 (2003).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijnders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Savas, "Useful genetic variation databases for oncologists investigating the genetic basis of variable treatment response and survival in cancer", Acta Oncol., 49(8):1217-26 (2010).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Simpson and Elias, "Isolating Fetal Cells from Maternal Blood", JAMA, 270(19):2357-61 (1993).

(56) References Cited

OTHER PUBLICATIONS

Simpson, "Is Cell-Free Fetal DNA from Maternal Blood Finally Ready for Prime Time?", Obst & Gynecol., 119(5):1-3 (2012).
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3_67-71 (1994).
Abadia-Molina, et al., "Immune phenotype and cytotoxic activity of lymploycytes from human term decidua against trophoblast", J. of Reproductive Immunology, n31:109-23 (1996).
Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63 (1979).
Batzer and Deininger, "ALU Repeats and Human Genomic Diversity", Nature, 3:370-79 (2002).
Bradstock, et al., "Functional and phenotypic assessment of neonatal human leucocytes expressing natural killer cell-associated antigen", Immunology and Cell Biology (71:535-42 (1993).
Campbell, et al., "Subclonal phylogenetic structures in cancer revealed by ultra-deep sequencing", PNAS, 105(35):13081-86 (2008).
Cicuttini and Boyd, "Hemopoietic and Lymphoid Progenitro Cells in Human Umbilical Cord Blood", Developmental Immunology, 4:1-11 (1994).
Datta, et al., "Sensitive Detection of Occult Breast Cancer by the Reverse-Transcriptase Polymerase Chain Reaction", J. of Clinical Oncology, 12(3): 475-82 (1994).
Dennin, "DNA of Free and Complexed Origin in Human Plasma: Concentration and Length Distribution", Klin. Wochenschr., 57:451-56 (1979).
Fisher, et al., "Genetic evidence that placental site trophoblastic tumours can originate from a hydatidiform mole or a normal conceptus", Br. J. Cancer, 65:355-358 (1992).
Fournie, et al., "Plasma DNA as Cell Death Marker in Elderly Patients", Gerontology, 39:215-221 (1993).
Geifman-Holzman, et al., "Fetal RhD genotyping in fetal cells flow sorted from maternal blood", Am. J. Obstet. Gynecol., 174(3):818-22 (1996).
Ghossein, et al.. "Detection of Circulating Tumor Cells in Patients With Localized and Metastatic Prostatic Carcinoma Clinical Implications", J. of Clin. Oncology, 13(5):1995-200 (1995).
Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Heid, et al., "Real Time Quantitative PCR", Genome Res., 6:986-94 (1996).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).
International Human Genome Sequencing Consortium, "Initial sequencing and analysis of the human genome", Nature, 409:860-921 (2001).
Kazakov, et al., "Extracellular DNA in the Blood of Pregnant Women", Tsitologiia (Cytology), 37(3):232-37 (1995).

Kogan, et al., "An improved method for prenatal diagnosis of genetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Margulies, et al., "Genome sequencing in microfabricated high-density picolitre reactors", Nature, 437(15):376-80 and errata (2005).
Mikhaylov, et al., "Synthesis and content of DNA in human decidual cells at various stages of differentiation according to flow cytometry analysis", Tsitologiia (Cytology), 34(6):67-72 (1992).
Nelson, et al., "Alu polymerase chain reaction: A method for rapid isolation of human-specific sequence from complex DNA sources, " PNAS USA, 86:6686-90 (1989).
Paolella, et al., "The Alu family repeat promoter has a tRNA-like bipartite structure", EMBO J., 2(5):691-96 (1983).
Oei, et al., "Clusters of regulatory signals for RNA polymerase II transcription associated with Alu family repeats and CpG islands in human promoters", Genomics, 83:873-82 (2004).
Robbins, et al., *Pathologic Basis of Disease 5th Ed.*, Chapter 23, pp. 1071-1088 (1994).
Ronaghi, et al., "A Sequencing Method Based on Real_Time Pyrophosphate", Science, 281:363-65 (1998).
Saiki, et al., "Primer-directed Enzymatic Amplification of DNA with a Thermostable DNA Polymerase", Science, 239:487-91 (1987).
Schallhammer, et al., "Phenotypic comparison of natural killer cells from peripheral blood and from early pregnancy decidua", Early Pregnancy: Biology and Medicine, 3:15-22 (1997).
Schroder, et al., "Transplacental passage of blood cells", J. of Medical Genetics, 12:230-42 (1974).
Shapiro, et al., "Determination of Circulating DNA Levels in Patients with Benign or Malignant Gastrointestinal Disease", Cancer, 51:2116-20 (1983).
Shendure, et al., "Accurate Multiplex Polony Sequencing of an Evolved Bacterial Genome", Science, 309:1728-32 (2005).
Simpson, et al., "Isolating Fetal Cells in Maternal Circulation for Prenatal Diagnosis", Prenatal Diagnosis, 14:1229-42 (1994).
Smith, et al.,"Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Sorenson, et al., "Soluble normal and mutated DNA sequences from single-copy genes in human blood", Cancer Epidemmiol. Biomarkers, 3:64-71 (1994).
Stroun, et al., "Circulating Nulceic Acids in Higher Organisms", Rev. Cytol. 51:1-48 (1977).
Stroun, et al., The Origin and Mechanism of Circulating DNA, Annals New York Academy of Sciences, 906:161-68 (2000).
Tagle, et al., "An optimized Alu-PCR primer pair for human-specific amplification of YACs and somatic cells hybrids", Human Molecular Genetics, 1(2):121-22 (1992).
International Search Report for PCT/US2011/046981, dated Oct. 15, 2012.
Stroun, et al., "Neoplastic Characteristics of the DNA Found in the Plasma of Cancer Patients", Oncology, 46: 318-322 (1989).
Stroun, et al., "Isolation and Characterization of DNA from the Plasma of Cancer Patients", Eur. J. Cancer Clin. Oncol., 23(6) 707-12 (1987).
Sullivan, et al., "Evidence for Structural Heterogeneity from Molecular Cytogenetic Analysis of Dicentric Robertsonian Translocations", Am. J. Hum. Genet., 59:167-75 (1996).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Systematic microarray-based identification of placental mRNA in maternal plasma: towards non-invasive prenatal gene expression profiling", J. Med Genet, 41:461-67 (2004).
Tsui, et al., "Noninvasive prenatal diagnosis of hemophilia by microfluidics digital PCR analysis of maternal plasma DNA", Blood, 117:3684=91 (2011).
Vogelstein, et al., "Digital PCR", PNAS USA, 96:9236-41 (1999).

(56) References Cited

OTHER PUBLICATIONS

Wachtel, et al., "Fetal cells in the maternal circulation: Isolation by multiparameter flow cytometry and confirmation by polymerase chain reaction", Human Reprod., 6(10):1466-69 (1991).
Wald, et al., "Maternal serum screening for Down's syndrome in early pregnancy", BMJ, 297:883-87 (1988).
Wald, et al., "Antenatal maternal serum screening for Down's syndrome: results of a demonstration project", BMJ, 305(6850):391-94 (1992).
Wang, et al., "PennCNV: An integrated hidden Markov model designed for high-resolution copy number variation detection in whole-genome SNP genotyping data", Genome Res., 17:1665-74 (2007).
Ward, et al., "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Wu and Wallace, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Lapair, et al., "Cell-Free DNA in Amniotic Fluid: Unique Fragmentation Signatures in Euploid and Aneuploid Fetuses", Clinical Chem., 53(3):405-11 (2007).
Search Report dated Jan. 20, 2012 for (PCT/US2012/21955).
Search Report dated May 2, 2012 for PCT/US2011/046935).
Search Report dated May 10, 2012 for (PCT/US2012/026754).
Search Report dated May 11, 2012 for (PCT/US2012/022261).
Bodurtha and Strauss, "Genomics and Prenatal Care", New Eng. J. of Medicine, 366:64-73 (2012).
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.
Sparks, et al., "Selective analysis of cell-free DNA in maternal blood for evaluation of fetal trisomy", Prenatal Diagnosis, 32:1-7 (2012).
Tomilin, et al., "Mechanisms of Chromosome Destabilization in Human Cells", Sov. Sci. Rev. D. Physiochem. Biol., 10:39-89 (1992).
Ulbright, "Germ cell tumors of the gonads: a selective review emphasizing problems in differential diagnosis, newly appreciated, and controversial issues," Modern Pathology, 18:S61-S79 (2005).
Vasioukhin, et al., "Point mutations in the N-ras gene in the blood plasma DNA of patients with myelodysplastic cyndrome or acute myelogenous leukaemia", British J. of Haematology, 86:774-79 (1994).
Walker, et al., "Human DNA quantitation using Alu element-based polymerase chain reaction", Analytical Biochem., 315:122-28 (2003).
Witt, et al., "An improved, non-isotopic method of screening cells from patients with abnormalities of sexual differentiation for Y chromosomal DNA content", J. Med. Genet., 30:304-07 (1993).
Xie and Tammi, "CNV-seq, a new method to detect copy number variation using high throughput sequencing", BMC Bioinformatics, 10:80 (2008), doi 10.1186/1471-2105-10-80, p. 1-9.
Search Report dated Feb. 21, 2013 for (PCT/US2011/046963), entire document.
Search Report dated Apr. 19, 2013 for (PCT/US2012/70177), entire document.
Office Action dated Apr. 15, 2013 for U.S. Appl. No. 13/356,133 (inventor A. Oliphant, filed Jan. 23, 2012), entire document.
Office Action dated May 17, 2013 for U.S. Appl. No. 13/356,575 (inventor A. Oliphant, filed Jan. 23, 2012), entire document.
Office Action dated Apr. 5, 2013 for U.S. Appl. No. 13/689,206 (inventor A. Oliphant, filed 39 Nov. 2012), entire document.
Final Office Action dated Jul. 8, 2013 for U.S. Appl. No. 13/689,206 (inventor A. Oliphant, filed 39 Nov 2012), entire document.
Office Action dated Jul. 5, 2012 for U.S. Appl. No. 13/013,732 (inventor A. Oliphant, filed Jun. 25, 2011), entire document.
Office Action dated Apr. 11, 2013 for U.S. Appl. No. 13/013,732 (inventor A. Oliphant, filed Jun. 25, 2011), entire document.
Office Action dated Jul. 8, 2013 for U.S. Appl. No. 13/205,490 (inventor A. Sparks, filed Aug. 8, 2011), entire document.
Office Action dated Mar. 28, 2013 for U.S. Appl. No. 13/687,169 (inventor A. Sparks, filed Nov. 28, 2012), entire document.
Office Action dated Feb. 28, 2013 for U.S. Appl. No. 13/205,570 (inventor A. Sparks, filed Aug. 8, 2011), entire document.
Office Action dated Mar. 14, 2013 for U.S. Appl. No. 13/687,025 (inventor A. Sparks, filed Nov. 28, 2012), entire document.
Office Action dated May 10, 2012 for U.S. Appl. No. 13/293,419 (inventor A. Sparks, filed Nov. 10, 2011), entire document.
Office Action dated Aug. 22, 2012 for U.S. Appl. No. 13/293,419 (inventor A. Sparks, filed Nov. 10, 2011), entire document.
Advisory Action dated Jan. 29, 2013 for U.S. Appl. No. 13/293,419 (inventor A. Sparks, filed Nov. 10, 2011), entire document.
Office Action dated Feb. 28, 2013 for U.S. Appl. No. 13/245,133 (inventor A. Oliphant, filed Sep. 26, 2011), entire document.
Office Action dated Jun. 13, 2013 for U.S. Appl. No. 13/316,154 (inventor A. Oliphant, filed Dec. 9, 2011), entire document.
Office Action dated Jun. 13, 2013 for U.S. Appl. No. 13/338,963 (inventor A. Oliphant, filed Dec. 28, 2011), entire document.
Office Action dated Feb. 15, 2013 for U.S. Appl. No. 13/689,417 (inventor A. Oliphant, filed Nov. 29, 2012), entire document.
Bianchi, et al., "Large Amounts of Cell-free DNAS Are Present in Amniotic Fluid", Clin. Chem., 47(10) 1867-69 (2001).
Chiu, et al., "Non-invasive prenatal diagnosis by single molecule counting technologies", Trends in Genomics, 25(7):324-31 (2009).
Hayden, et al., "Multiplex-Ready PCR: A new method for multiplexed SSR and SNP genotyping", BMC Genomics, 9:80:1-12 (2007).
Hsuih, et al., "Novel, ligation-depdent PCR assay for detection of hepatitis C in serum", J. of Clin. Microbiology, 34(3):501-07 (1996).
Huang, et al., "Identification of a family of alternatively splied mRNA species of angiopoietin-1", Blood, 95:1993-99 (2000).
Indolfi, et al., "Perinatal Transmission of Hepatitis C Virus Infection", J. Med. Virol., 81:836-43 (2009).
Mardis, et al., "The impact of next-generation sequencing technology on genetics", Trends in Genetics, 24(3):133-41 (2007).
Porreca, et al., "Multiplex amplification of large sets of human exons", Nat. Methods, 4(11):931-36 (2007).
Schouten, et al., "Relative quantification of 40 nucleic acid sequences by multiplex ligation-dependent probe amplification", Nuc. Ac. Res., 30(12):e57 (2002).
Tewhey, et al., "Microdroplet-based PCR enrichment for large-scale targeted sequencing", Nat. Biotech., 27(11):1025-31 (2009).
Zolotukhina, et al., "Analysis of Cell-free DNA in Plasma and Serum of Pregnant Women", J. of Hist. and Cytochem., 53:297-99 (2005).
Office Action dated Oct. 31, 2013 for U.S. Appl. No. 13/356,575, filed Jan. 23, 2012, inventor Oliphant, entire document.
Office Action dated Jun. 25, 2014 for U.S. Appl. No. 13/689,206, filed Nov. 29, 2012, inventor Oliphant, entire document.
Office Action dated Feb. 11, 2014 for U.S. Appl. No. 13/689,206, filed Nov. 29, 2012, inventor Oliphant, entire document.
Office Action dated Jun. 26, 2014 for U.S. Appl. No. 13/356,133, filed Jan. 23, 2012, inventor Oliphant, entire document.
Office Action dated Oct. 18, 2013 for U.S. Appl. No. 13/356,133, filed Jan. 23, 2012, inventor Oliphant, entire document.
Office Action dated Jul. 31, 2013 for U.S. Appl. No. 13/013,732, filed Jun. 25, 2011, inventor Oliphant, entire document.
Office Action dated Apr. 14, 2014 for U.S. Appl. No. 13/013,732, filed Jun. 25, 2011, inventor Oliphant, entire document.
Office Action dated Feb. 11, 2014 for U.S. Appl. No. 13/405,839, filed Feb. 27, 2012, inventor Oliphant, entire document.

(56) References Cited

OTHER PUBLICATIONS

Office Action dated Jan. 31, 2014 for U.S. Appl. No. 13/605,505, filed Sep. 6, 2012, inventor Struble, entire document.
Office Action dated Aug. 8, 2013 for U.S. Appl. No. 13/605,505, filed Sep. 6, 2012, inventor Struble, entire document.
Office Action dated Aug. 30, 2013 for U.S. Appl. No. 13/687,169, filed Nov. 28, 2012, inventor Sparks, entire document.
Office Action dated May 8, 2014 for U.S. Appl. No. 13/687,169, filed Nov. 28, 2012, inventor Sparks, entire document.
Office Action dated Dec. 10, 2013 for U.S. Appl. No. 13/205,490, filed Aug. 8, 2011, inventor Sparks, entire document.
Office Action dated Jul. 8, 2013 for U.S. Appl. No. 13/205,490, filed Aug. 8, 2011, inventor Sparks, entire document.
Office Action dated Oct. 2, 2013 for U.S. Appl. No. 13/687,025, filed Nov. 28, 2012, inventor Sparks, entire document.
Office Action dated Jul. 16, 2014 for U.S. Appl. No. 13/687,025, filed Nov. 28, 2011, inventor Sparks, entire document.
Office Action dated Aug. 30, 2013 for U.S. Appl. No. 13/205,570, filed Aug. 8, 2011, inventor Sparks, entire document.
Office Action dated May 8, 2014 for U.S. Appl. No. 13/205,570, filed Aug. 8, 2011, inventor Sparks, entire document.
Office Action dated Jul. 14, 2014 for U.S. Appl. No. 13/293,419, filed Nov. 10, 2011, Sparks, entire document.
Office Action dated Jun. 26, 2014 for U.S. Appl. No. 13/205,603, filed Aug. 8, 2011, inventor Sparks, entire document.
Office Action dated Dec. 30, 2013 for U.S. Appl. No. 13/205,603, filed Aug. 8, 2011, inventor Sparks, entire document.
Office Action dated Dec. 11, 2013 for U.S. Appl. No. 13/274,309, filed Oct. 15, 2011, inventor Struble, entire document.
Office Action dated Aug. 30, 2013 for U.S. Appl. No. 13/245,133, filed Sep. 26, 2011, inventor Oliphant, entire document.
Office Action dated Feb. 28, 2013 for U.S. Appl. No. 13/245,133, filed Sep. 26, 2011, inventor Oliphant, entire document.
Office Action dated May 8, 2014 for U.S. Appl. No. 13/245,133, filed Sep. 26, 2011, inventor Oliphant, entire document.
Office Action dated May 12, 2014 for U.S. Appl. No. 13/689,417, filed Nov. 29, 2012, inventor Oliphant, entire document.
Office Action dated Oct. 31, 2013, filed Dec. 9, 2011, inventor Oliphant for U.S. Appl. No. 13/316,154, entire document.
Australian Patent Examination Report No. 1 dated Feb. 20, 2014 for 2011285512, entire document.
Australian Patent Examination Report No. 1 dated Mar. 4, 2014 for 2011285518, entire document.
Australian Patent Examination Report No. 1 dated Feb. 7, 2014 for 2011285477, entire document.
EPO Examination Report dated Nov. 21, 2013 for App. No. 11745880.2, entire document.
EPO Examination Report dated Nov. 21, 2013 for App. No. 11745881.1, entire document.
EPO Examination Report dated Nov. 28, 2013 for App. No. 11745883.6, entire document.
Search Report dated Sep. 12, 2013 for PCT/US 2012/026754, entire document.
Search Report dated Nov. 15, 2013 for PCT/US 2013/51310, entire document.
Search Report dated May 14, 2013 for PCT/US 2014/17092, entire document.
Tewhey, R. et al. (2009, e-published Nov. 1, 2009). "Microdroplet-based PCR enrichment for large-scale targeted sequencing," Nat Biotechnol 27(11):1025-1031; Supplementary materials: 26 pages.
Avent, N.D. et al. (2008). "RHD genotyping from maternal plasma: guidelines and technical challenges," Methods Mol Biol 444:185-201.
Boyle, E.A. et al. (Sep. 15, 2014, e-published May 26, 2014). "MIPgen: optimized modeling and design of molecular inversion probes for targeted resequencing," Bioinformatics 30(18):2670-2672.
Hardenbol, P. et al. (Jun. 2003, e-published May 5, 2003). "Multiplexed genotyping with sequence-tagged molecular inversion probes," Nat Biotechnol 21(6):673-678.
Mamanova, L. et al. (Feb. 2010). "Target-enrichment strategies for next-generation sequencing," Nat Methods 7(2):111-118.
Myllykangas, S. et al. (2010). "Targeted deep resequencing of the human cancer genome using next-generation technologies," Biotechnol Genet Eng Rev 27:135-158.
Shen, R. et al. (Jun. 2005). "High-throughput SNP genotyping on universal bead arrays," Mutation Research 573(1-2):70-82.
Turner, E.H. et al. (May 2009, e-published Apr. 6, 2009). "Massively parallel exon capture and library-free resequencing across 16 genomes," Nat Methods 6(5):315-316.
Agostini, et al., "Circulating cell-free DNA: a promising marker of pathologic tumor response in rectal cancer patients receiving preoperative chemotherapy", Ann. Surg. Oncol., 18(9):2461-68 (2011).
Arnheim, et al., "Molecular evidence for genetic exchanges among ribosomal genes on nonhomologous chromosomes in man and apes", PNAS USA, 77(12):7323-27 (1980).
Bandyopadhyay, et al, "Identification and characterization of satellite III subfamilies to the acrocentric chromosomes", Chromosome Research, 9:223-33 (2001).
Bianchi, "Prenatal diagnosis by analysis of fetal cells in maternal blood", J. of Pediatrics, 127(6):847-56 (1995).
Bianchi, "Isolation of fetal DNA from nucleated erythrocytes in maternal blood", PNAS USA, 87:3279-83 (1990).
Bianchi, "PCR Quantitation of Fetal Cells in Maternal Blood in Normal and Aneuploid Pregnancies", Am J. Hum. Genet., 61:822-29 (1997).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bombard, et al., "Fetal RHD genotype detection from circulating cell-free DNA in maternal plasma in non-sensitized RhD negative women", Prenat Diagn, 31:802-08 (2011).
Camaschella, et al., "Prenatal Diagnosis of Fetal Hemoglobin Lepore-Boston Disease on Maternal Peripheral Blood", Blood, 75(11):2102-06 (1990).
Cappuzzo, et al., "Epidermal growth factor receptor gene and protein and gefitinib sensitivity in non-small-cell lung cancer", J. Natl Cancer Inst., 97(9):643-55 (2005).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011).
Chim, et al., "Detection of the placental epigenetic signature of the maspin gene in maternal plasma", PNAS USA, 102(41):14753-58 (2005).
Chiu, et al, "Effects of Blood-Processing Protocols on Fetal and Total DNA Quantification in Maternal Plasma", Clin. Chem., 47(9):1607-1613 (2001).
Chiu, el al., "Maternal plasma DNA analysis with massively parallel sequencing by ligation for noninvasive prenatal diagnosis of trisomy 21", 56:459-63 (2010).
Chiu, el al, "Noninvasive prenatal diagnosis of fetal chromosomal aneuploidy by massively parallel genomic sequencing of DNA in maternal plasma", PNAS USA 105:20458-63 (2008).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Non-invasive prenatal assessment of trisomy 21 by multiplexed maternal plasma DNA sequencing: large scale validity study", Br Med J. 342:c7401 (2011).
Cirigiliano, et al., "Clinical application of multiplex quantitative fluorescent polymerase chain reaction QF-PCR for the rapid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Choo, et al., "A homologous subfamily of satellite III DNA on human chromosomes 14 and 22", Nucleic Acids Research, 18(19):5641-47 (1990).

(56) References Cited

OTHER PUBLICATIONS

Choo, et al., "A Chromosome 14-specific Human Satellite III DNA Subfamily That Shows Variable Presence on Different Chromosomes 14", Am J. Hum. Genet., 50:706-16 (1992).
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cockwell, et al., "Distribution of the D15A1 copy number polymorphism", European J. of Hum. Genet., 15:441-45 (2007).
Conover, Practical Nonparametric Statistics, pp. 295-301 (John Wiley & Sons, NY)(1971).
Costa, et al., "New strategy for prenatal diagnosis of X-linked disorders", N. Engl J. Med., 346:1502 (2002).
Dear, et al., "A High-Resolution Metric Happy Map of Human Chromosome 14" Genmoics, 48 232-41 (1998).
Dhallan, et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer", Ginekol Pol. 81(6):422-25 (2010).
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian Translocations", Am J. Hum Genet., 50:717-24 (1992).
Enrich, et al., "Noninvasive detection of fetal trisomy 21 by sequencing of fetal DNA in maternal blood: a study in a clinical setting", Am J. Obstet Gynecol, 2011:204:205 e1-11 (2011).
Fan, et al., "Noninvasive diagnosis of fetal aneuploidy by shotgun sequencing DNA from maternal blood", PNAS USA, 105(42):16266-71 (2008).
Fan, et al., "Analysis of the Size Distributions of Fetal and Maternal Cell-Free DNA by Paired-End Sequencing", Clin. Chem., 56(8):1279-80 (2010).
Fan, et al., "Sensitivity of noninvasive prenatal detection of fetal aneuploidy from maternal plasma using shotgun sequencing is limited only by counting statistics", PLoS One, 5:e10439 (2010).
Fejgin, et al., "Fetal cells in the uterine cervix: a source for early non-invasive prenatal diagnosis", Prenat. Diag., 21:619-21 (2001).
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fowke, Genetic analysis of human DNA recovered from minute amounts of serum and plasma, J. of Immunol. Meth., 180:45-51 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Greeley, et al., "Get ready for the flood of fetal gene screening", Nature, 469:289-91 (2011).
Guatelli, et al., "Isothermal, in vitro amplification of nucleic acids by a multienzyme reaction modeled after retroviral replication", PNAS USA, 87(5):1874-(1990).
Han, et al, "Molecular Chytogenetic Characterization of 17 rob(13q14q) Robertsonian Translocations by Fish, Narrowing the Region Containing the Breakpoints", Am J. Hum. Genet., 55:960-67 (1994).
Harrell, Regression modeling strategies, §§ 9.2.2 and 1.10.5 (Springer Vertag)(2001).
Alexandrov, et al., (May 11, 1993). "Definition of a new alpha satellite suprachromosomal family characterized by monomeric organization", Nucleic Acids Research, 21(9):2209-2215.
Chromosome 14 Map (Mar. 14, 1996). The Genethon Human Genetic Linkage Map, Collections, Supplements, *Nature*, 3 pages.

* cited by examiner

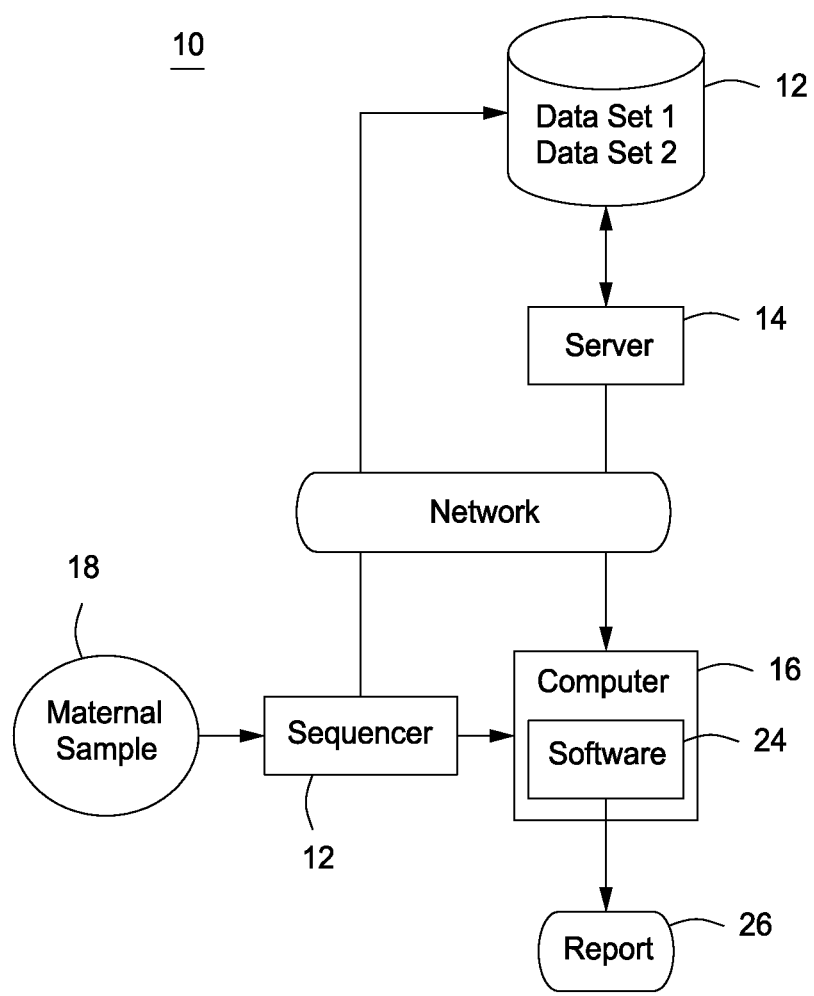

DETECTION OF GENETIC ABNORMALITIES

CROSS-REFERENCE TO RELATED APPLICATIONS

The present application claims priority to U.S. Provisional Application Ser. No. 61/448,067 filed Mar. 1, 2011, and is a continuation-in-part of U.S. Ser. No. 13/013,732, filed Jan. 25, 2011; Ser. No. 13/205,490, filed Aug. 8, 2011; Ser. No. 13/205,570, filed Aug. 8, 2011 and Ser. No. 13/205,603, filed Aug. 8, 2011, each of which claims priority to U.S. Ser. No. 61/371,605, filed Aug. 6, 2010, each of which are incorporated by reference in their entirety.

FIELD OF THE INVENTION

This invention relates to diagnosis of genetic abnormalities and assay systems for such diagnosis.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genetic abnormalities account for a wide number of pathologies, including pathologies caused by chromosomal aneuploidy (e.g., Down's syndrome), germline mutations in specific genes (e.g., sickle cell anemia), and pathologies caused by somatic mutations (e.g., cancer). Diagnostic methods for determining such genetic anomalies have become standard techniques for identifying specific diseases and disorders, as well as providing valuable information on disease source and treatment options.

For example, prenatal screening and diagnosis are routinely offered in antenatal care and are considered to be important in allowing women to make informed choices about pregnancies affected by genetic conditions. Conventional methods of prenatal diagnostic testing currently requires removal of a sample of fetal cells directly from the uterus for genetic analysis, using either chorionic villus sampling (CVS) typically between 11 and 14 weeks gestation or amniocentesis typically after 15 weeks. However, these invasive procedures carry a risk of miscarriage of around 1%. Mujezinovic and Alfirevic, Obstet Gynecol 2007; 110:687-694.

Although these approaches to obtaining fetal DNA currently provides the gold standard test for prenatal diagnosis, many women decide not to undergo invasive testing, primarily because it is unpleasant and carries a small but significant risk of miscarriage. A reliable and convenient method for non-invasive prenatal diagnosis has long been sought to reduce this risk of miscarriage and allow earlier testing. Although some work has investigated using fetal cells obtained from the cervical mucus (Fejgin M D et al., Prenat Diagn 2001;21:619-621; Mantzaris et al., ANZJOG 2005; 45:529-532), most research has focused on strategies for detecting genetic elements from the fetus present in the maternal circulation. It has been demonstrated that there is bidirectional traffic between the fetus and the mother during pregnancy (Lo et al., Blood 1996; 88:4390-4395), and multiple studies have shown that both intact fetal cells and cell-free fetal nucleic acids cross the placenta and circulate in the maternal bloodstream (See, e.g., Chiu R W and Lo Y M, Semin Fetal Neonatal Med. 2010 Nov. 11).

There is thus a need for non-invasive methods of screening for genetic abnormalities, including aneuploidies, in mixed samples comprising normal and putative abnormal DNA. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides assay systems and related methods for determining genetic abnormalities in mixed samples comprising genomic material (e.g., cell free DNA) from both normal and putative genetically atypical cells. Exemplary mixed samples for analysis using the assay systems of the invention include samples comprising both maternal and fetal cell free DNA and samples that contain cell free DNA from normal cells and circulating cancerous cells.

In one aspect, the assay system utilizes enrichment and detection of selected nucleic acid regions in cell free DNA in a mixed sample to identify the presence or absence of a chromosomal aneuploidy. Levels of selected nucleic acid regions can be determined for a genomic region of interest (e.g., a chromosome or a portion thereof) and compared to the quantities of nucleic acid regions of one or more other genomic regions of interest and/or one or more reference genomic regions to detect potential aneuploidies based on chromosome frequencies in the mixed sample.

In one general aspect, the invention provides an assay system for detection of a copy number variation in a genomic region of interest in a mixed sample, comprising the steps of providing a mixed sample comprising cell free DNA from a mixed sample, enriching for two or more selected nucleic acid regions from a first genomic region of interest in the mixed sample; enriching for two or more selected nucleic acid regions from a second genomic region of interest in the mixed sample, determining the relative frequency of the selected regions from the first and second genomic regions of interest, comparing the relative frequency of the selected regions from the first and second genomic region of interest, and identifying the presence or absence of a copy number variation based on the compared relative frequencies of the selected regions.

In one general aspect, the invention provides an assay system for detection of the presence or absence of an aneuploidy in a genomic region, comprising the steps of providing a mixed sample comprising cell free DNA from normal and putative abnormal cells, enriching for two or more selected nucleic acid regions from a first chromosome of interest in the mixed sample; enriching for two or more selected nucleic acid regions from a second chromosome of interest in the mixed sample, determining the relative frequency of the selected regions from the first and second chromosomes of interest, comparing the relative frequency of the selected regions from the first and second chromosomes of interest, and identifying the presence or absence of an aneuploidy based on the compared relative frequencies of the selected regions.

In another general aspect, the invention provides an assay system for detection of the presence or absence of an aneuploidy, comprising the steps of providing a mixed sample comprising cell free DNA from normal and putative abnormal cells, amplifying two or more selected nucleic acid regions from a first chromosome of interest in the mixed sample; amplifying two or more selected nucleic acid regions from a second chromosome of interest in the mixed sample, determining the relative frequency of the selected regions from the first and second chromosomes of interest, comparing the relative frequency of the selected regions from the first and second chromosomes of interest, and identifying the presence or absence of an aneuploidy based on the compared relative frequencies of the selected regions. In a specific aspect, the nucleic acid regions of the first and second chromosomes are amplified in a single reaction, and preferably in a single reaction contained within a single vessel.

In a related aspect, the selected nucleic acids analyzed using the assay system of the invention can be amplified using universal amplification methods following the initial selective amplification or enrichment from the mixed sample. The use of universal amplification allows multiple nucleic acids regions from a single or multiple sample to be amplified using a single or limited number of amplification primers, and is especially useful in amplifying multiple selected regions in a single reaction.

Thus, in a preferred aspect of the invention, sequences complementary to primers for use in universal amplification are introduced to the selected nucleic acid regions during or following selective amplification or enrichment. Preferably such sequences are introduced to the ends of such selected nucleic acids, although they may be introduced in any location that allows identification of the amplification product from the universal amplification procedure.

Preferably, the assay system detects the presence or absence of genetic abnormalities in samples that can be easily obtained from a subject, such as blood, plasma, serum and the like. In one general aspect, the assay system utilizes detection of selected regions in cell free DNA in a mixed sample to identify the presence or absence of a copy number variation in a genomic region of interest. In one more specific aspect, the assay system utilizes detection of selected regions in cell free DNA in a mixed sample to identify the presence or absence of a chromosomal aneuploidy. The quantities of selected nucleic acid regions can be determined for a genomic region of interest and compared to the quantities of selected nucleic acid regions from another genomic region of interest and/or to the quantities of selected nucleic acid regions from a reference genomic region of interest to detect potential aneuploidies based on chromosome frequencies in the mixed sample. In a particular aspect, the ratio of the frequencies of the nucleic acid are compared to a reference mean ratio that has been determined for a statistically significant population of genetically "normal" subjects, i.e. subjects that do not have the particular genetic anomaly that is being interrogated in a particular assay system.

It is a feature of the present invention that the nucleic acid regions are determined using non-polymorphic detection methods, i.e., detection methods that are not dependent upon the presence or absence of a particular polymorphism to identify the selected nucleic acid region. In a preferred aspect, the assay detection systems utilize non-polymorphic detection methods to "count" the relative numbers of selected nucleic acid regions present in a mixed sample. These numbers can be utilized to determine if, statistically, a mixed sample is likely to have a copy number variation in a genomic region. Similarly, these numbers can be utilized to determine, if statistically, one of the DNA origins of a mixed sample is likely to have an abnormal copy number polymorphism. Such information can be used to identify a particular pathology or genetic disorder, to confirm a diagnosis or recurrence of a disease or disorder, to determine the prognosis of a disease or disorder, and/or to assist in determining potential treatment options.

In some aspects, the relative frequencies of selected nucleic acid regions from different chromosomes in a sample are individually quantified and compared to determine the presence or absence of an aneuploidy in a mixed sample. The individually quantified regions may undergo a normalization calculation or the data may be subjected to outlier exclusion prior to comparison to determine the presence or absence of an aneuploidy in a mixed sample. In other aspects, the relative frequencies of the selected nucleic acid regions are used to determine a chromosome frequency of the first and second chromosomes of interest, and the presence or absence of an aneuploidy is based on the compared chromosome frequencies of the first and second chromosomes of interest. In yet other aspects, the relative frequencies of the selected nucleic acid regions are used to determine a chromosome frequency of a chromosome of interest and a reference chromosome, and the presence or absence of an aneuploidy is based on the compared chromosome frequencies of the chromosome of interest and the reference chromosome.

The assay system of the invention can be configured as a highly multiplexed system which allows for multiple nucleic acid regions from a single or multiple chromosomes within an individual sample and/or multiple samples to be analyzed simultaneously. In such multiplexed systems, the samples can be analyzed separately, or they may be initially pooled into groups of two or more for analysis of larger numbers of samples. When pooled data is obtained, such data is preferably identified for the different samples prior to analysis of aneuploidy. In some aspects, however, the pooled data may be analyzed for potential aneuploidies, and individual samples from the group subsequently analyzed if initial results indicates that a potential aneuploidy is detected within the pooled group.

In certain aspects, the assay systems utilize one or more indices that provide information on specific samples or loci. For example, a primer that is used in selective amplification may have additional sequences that are specific to the locus, e.g., a nucleic acid tag sequence that is indicative of the selected nucleic acid region or a particular allele of that nucleic acid region. In another example, an index is used in selective or universal amplification that is indicative of a sample from which the nucleic acid was amplified. In yet another example, a unique identification index is used to distinguish a particular amplification product from other amplification products obtained from the detection methods. A single index may also be combined with any other index to create one index that provides information for two properties (e.g., sample-identification index, allele-locus index).

In one particular aspect, the method of the invention generally comprises detection of the number of copies of two or more selected nucleic acid regions on a first chromosome and two or more selected nucleic acid regions corresponding to a second chromosome, and comparison of the quantities of the selected nucleic acids in a maternal sample to identify the presence or absence of fetal aneuploidy. The selected nucleic acid regions can be isolated from the maternal sample using any means that selectively isolate the particular nucleic acids present in the maternal sample for analysis, e.g., hybridization, amplification or other form of sequence-based isolation of the nucleic acids from the maternal sample. Following isolation, the selected target nucleic acids are individually distributed in a suitable detection format, e.g., on a microarray or in a flow cell, for determination of the relative quantities of each selected nucleic acid in the maternal sample. The relative quantities of the detected nucleic acids are indicative of the number of copies of chromosomes that correspond to the target nucleic acids present in the maternal sample.

Following isolation and distribution of the target nucleic acids in a suitable format, the target sequences are identified, e.g., through sequence determination of the target sequence itself via detection of an associated index (e.g., an identification index, a locus index, an allele index and the like), or via sequence determination and detection of an associated index.

In one specific aspect, the invention provides an assay system for detection of the presence or absence of a fetal aneuploidy, comprising the steps of providing a maternal sample comprising maternal and fetal cell free DNA, amplifying two or more selected nucleic acid regions from a first and second chromosome of interest in the maternal sample, amplifying two or more selected nucleic acid regions from the first and second chromosome of interest in the maternal sample, determining the relative frequency of the selected regions from the chromosomes of interest, comparing the relative frequency of the selected nucleic acid regions from the first and second chromosomes of interest, and identifying the presence or absence of a fetal aneuploidy based on the compared relative frequencies of the selected nucleic acid regions.

In some specific aspects, the relative frequencies of the nucleic acid regions are individually calculated, and the relative frequencies of the individual nucleic acid regions are compared to determine the presence or absence of a fetal aneuploidy. In other specific aspects, the relative frequencies of the selected regions are used to determine a chromosome frequency of the first and second chromosomes of interest and the reference chromosome, and the presence or absence of a fetal aneuploidy is based on the compared chromosome frequencies of the first and second chromosomes of interest.

In another specific aspect, the invention provides an assay system for detection of the presence or absence of a fetal aneuploidy, comprising the steps of providing a maternal sample comprising maternal and fetal cell free DNA, amplifying two or more selected nucleic acid regions from a chromosome of interest in the maternal sample, amplifying two or more selected nucleic acid regions from a reference chromosome in the maternal sample, determining the relative frequency of the selected regions from the chromosomes of interest and the reference chromosome, comparing the relative frequency of the selected nucleic acid regions from the chromosomes of interest and the reference chromosome, and identifying the presence or absence of a fetal aneuploidy based on the compared relative frequencies of the selected nucleic acid regions. In some specific aspects, the relative frequencies of the nucleic acid regions are individually calculated, and the relative frequencies of the individual nucleic acid regions are compared to determine the presence or absence of a fetal aneuploidy. In other specific aspects, the relative frequencies of the nucleic acid regions are used to determine a chromosome frequency of the chromosome of interest and the reference chromosome, and the presence or absence of a fetal aneuploidy is based on the compared chromosome frequencies of the chromosome of interest and the reference chromosome.

The maternal sample used for analysis can be obtained or derived from any sample which contains the DNA of interest to be analyzed using the assay system of the invention. For example, a maternal sample may be from any maternal fluid which comprises both maternal and fetal cell free DNA, including but not limited to maternal plasma, maternal serum, or maternal blood.

It is a feature of the invention that the nucleic acids analyzed in the assay system do not require polymorphic differences between the fetal and maternal sequences to determine potential aneuploidy. It is another feature of the invention that the substantial majority of the nucleic acids isolated from the maternal sample and detected in the assay system provide information relevant to the presence and quantity of a particular chromosome in the maternal sample, i.e. the detected target nucleic acids are indicative of a particular nucleic acid region associated with a chromosome. This ensures that the majority of nucleic acids analyzed in the assay system of the invention are informative.

In some aspects, multiple nucleic acid regions are determined for each genomic region under interrogation, and the quantity of the selected regions present in the maternal sample are individually summed to determine the relative frequency of a nucleic acid region in a maternal sample. This includes determination of the frequency of the nucleic acid region for the combined maternal and fetal DNA present in the maternal sample. Preferably, the determination does not require a distinction between the maternal and fetal DNA, although in certain aspects this information may be obtained in addition to the information of relative frequencies in the sample as a whole.

In preferred aspects, target nucleic acids corresponding to multiple nucleic acid regions from a chromosome are detected and summed to determine the relative frequency of a chromosome in the maternal sample. Frequencies that are higher than expected for a nucleic acid region corresponding to one chromosome when compared to the quantity of a nucleic acid region corresponding to another chromosome in the maternal sample are indicative of a fetal aneuploidy. This can be comparison of chromosomes that each may be a putative aneuploid in the fetus (e.g., chromosomes 18 and 21), where the likelihood of both being aneuploid is minimal. This can also be a comparison of chromosomes where one is putatively aneuploid (e.g., chromosome 21) and the other acts as a reference chromosome (e.g. an autosome such as chromosome 2). In yet other aspects, the comparison may utilize two or more chromosomes that are putatively aneuploid and one or more reference chromosomes.

In one aspect, the assay system of the invention analyzes multiple nucleic acids representing selected loci on chromosomes of interest, and the relative frequency of each selected locus from the sample is analyzed to determine a relative chromosome frequency for each particular chromosome of interest in the sample. The chromosomal frequency of two or more chromosomes is then compared to statistically determine whether a chromosomal abnormality exists.

In another aspect, the assay system of the invention analyzes multiple nucleic acids representing selected loci on chromosomes of interest, and the relative frequency of each selected nucleic acid from the sample is analyzed and independently quantified to determine a relative amount for each selected locus in the sample. The sum of the loci in the sample is compared to statistically determine whether a chromosomal aneuploidy exists.

In another aspect, subsets of loci on each chromosome are analyzed to determine whether a chromosomal abnormality exists. The loci frequency can be summed for a particular chromosome, and the summations of the loci used to determine aneuploidy. This aspect of the invention sums the frequencies of the individual loci on each chromosome and then compares the sum of the loci on one chromosome against another chromosome to determine whether a chromosomal abnormality exists. The subsets of loci can be chosen randomly but with sufficient numbers of loci to yield a statistically significant result in determining whether a chromosomal abnormality exists. Multiple analyses of different subsets of loci can be performed within a mixed sample to yield more statistical power. In another aspect, particular loci can be selected on each chromosome that are known to have less variation between maternal samples, or by limiting the data used for determination of chromosomal frequency, e.g., by ignoring the data from loci with very high or very low frequency within a sample.

In a particular aspect, the measured quantity of one or more particular loci on a chromosome is normalized to account for differences in loci quantity in the sample. This can be done by normalizing for known variation from sources such as the assay system (e.g. temperature, reagent lot differences), underlying biology of the sample (e.g. nucleic acid content), operator differences, or any other variables.

In certain specific aspects, determining the relative percentage of fetal DNA in a maternal sample may be beneficial in performing the assay system, as it will provide important information on the relative statistical presence of nucleic acid regions that may be indicative of fetal aneuploidy. In each maternally-derived sample, the fetus will have 50% of its loci inherited from the mother and 50% of the loci inherited from the father when no copy number variant is present for that locus. Determining the loci contributed to the fetus from paternal sources (e.g., through identification of Y-specific sequences or polymorphisms) can allow the estimation of fetal DNA in a maternal sample, and thus provide information used to calculate the statistically significant differences in chromosomal frequencies for chromosomes of interest. Such loci could thus provide two forms of information in the assay—allelic information can be used for determining the percent fetal DNA contribution in a maternal sample and a summation of the allelic information can be used to determine the relative overall frequency of that locus in a maternal sample. The allelic information is not needed to determine the relative overall frequency of that locus.

Thus, in some specific aspects, the relative fetal contribution of maternal DNA at the allele of interest can be compared to the paternal contribution at that allele to determine approximate fetal DNA concentration in the sample. In a particular aspect, the estimation of fetal DNA in a maternal sample is determined at those loci where the mother is homozygous at the locus for a given allele and a different allele is inherited by the fetus from the father at that locus. In this situation, the fetal DNA amount will approximately be twice amount of the fetal allele inherited from the father. In other specific aspects, the relative quantity of solely paternally-derived sequences (e.g., Y-chromosome sequences or paternally-specific polymorphisms) can be used to determine the relative concentration of fetal DNA in a maternal sample.

In a specific aspect, the assay system of the invention can be utilized to determine if one or more fetus in a multiples pregnancy is likely to have an aneuploidy, and whether further confirmatory tests should be undertaken to confirm the identification of the fetus with the abnormality. For example, the assay system of the invention can be used to determine if one of two twins has a high likelihood of an aneuploidy, followed by a more invasive technique that can distinguish physically between the fetuses, such as amniocentesis or chorionic villi sampling, to determine the identification of the affected fetus.

In another specific aspect, the assay system of the invention can be utilized to determine if a fetus has a potential mosaicism, and whether further confirmatory tests should be undertaken to confirm the identification of mosaicism in the fetus. Mosaicism could be subsequently confirmed using other testing methods that could distinguish mosaic aneuploidy in specific cells or tissue, either prenatally or postnatally.

In another aspect, the oligonucleotides for a given target nucleic acid can be connected at the non-sequence specific ends such that a circular or unimolecular probe may bind thereto. In this aspect, the 3' end and the 5' end of the circular probe binds to the target sequence and at least one universal amplification region is present in the non-target specific sequence of the circular probe.

In certain aspects, the assay format allows the detection of a combination of abnormalities using different detection mechanisms applied to the maternal sample. For example, fetal aneuploidy can be determined through the identification of selected target nucleic acids in a maternal sample, and specific mutations may be detected by sequence determination of mutations in one or more identified alleles of a known locus. Thus, in specific aspects, sequence determination of a target nucleic acid can provide information on the number of copies of a particular locus in a maternal sample as well as the presence of a mutation in a fetal allele within the maternal sample.

In some aspects, the assay system is used for both the detection of the presence or absence of fetal aneuploidy and determination of maternal and or fetal carrier status for an allele of interest. Such assays comprise the steps of providing a maternal sample comprising cell free DNA, amplifying two or more selected nucleic acid regions from a first chromosome of interest in the maternal sample, amplifying two or more selected nucleic acid regions from a second chromosome of interest in the maternal sample, amplifying one or more selected nucleic acid regions comprising an allele of interest in the maternal sample, detecting the amplified nucleic acid regions, quantifying the relative frequency of the selected nucleic acid regions from the first and second chromosomes of interest, comparing the relative frequency of the selected nucleic acid regions from the first and second chromosomes of interest, and identifying the presence or absence of a genetic alteration based on the compared relative frequencies of the first and second chromosome of interest.

In specific aspects, the assay system is used for both the detection of the presence or absence of fetal aneuploidy and determination of maternal and or fetal carrier status for genetic alterations in a locus associated with a heritable disease. The assay system comprises providing a mixed sample comprising cell free DNA, amplifying two or more selected nucleic acid regions from a first chromosome of interest in the mixed sample, amplifying two or more selected nucleic acid regions from a second chromosome of interest in the mixed sample, amplifying one or more nucleic acid region comprising all or part of a locus associated with a heritable disease, detecting the amplified nucleic acid regions, quantifying the relative frequency of the selected nucleic acid regions from the first and second chromosomes of interest, comparing the relative frequency of the selected nucleic acid regions from the first and second chromosomes of interest, identifying the presence or absence of fetal aneuploidy based on the compared relative frequencies of the first and second chromosome of interest, detecting the presence or absence of any genetic alterations in the one or more nucleic acid region comprising all or part of a locus associated with a heritable disease, and quantifying the frequency of nucleic acid regions comprising any genetic alterations to determine maternal and/or fetal carrier status.

In these assay systems, relative frequencies of the selected nucleic acid regions can be individually quantified, and the relative frequencies of the individual nucleic acid regions compared to determine the presence or absence of a genetic alteration in the fetal or maternal DNA. Such quantified relative frequencies of the selected nucleic acid regions are optionally normalized following detection and prior to quantification.

In specific aspects, the selected nucleic acid regions are associated with one or more identifying indices, and the frequency of the selected nucleic acid regions can be determined through identification of the associated one or more indices.

In preferred aspects, the nucleic acid regions are assayed in a single vessel, and the nucleic acid regions undergo a universal amplification. In other preferred aspects, the selected nucleic acid regions are each counted an average of at least 500 times.

The maternal sample for determining carrier status can be maternal blood, maternal plasma or maternal serum. Preferably it is maternal serum.

These and other aspects, features and advantages will be provided in more detail as described herein.

DESCRIPTION OF THE FIGURES

FIG. 1 is a block diagram illustrating an exemplary system environment.

DETAILED DESCRIPTION OF THE INVENTION

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Gait, "Oligonucleotide Synthesis: A Practical Approach" IRL Press, London (1984); Nelson and Cox, *Lehninger, Principles of Biochemistry*, $3^{rd}$ Ed., W. H. Freeman Pub., New York (2000); and Berg et al., *Biochemistry*, $5^{th}$ Ed., W.H. Freeman Pub., New York (2002), all of which are herein incorporated by reference in their entirety for all purposes.

Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "and," and "the" include plural referents unless the context clearly dictates otherwise. Thus, for example, reference to "a nucleic acid region" refers to one, more than one, or mixtures of such regions, and reference to "an assay" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein are incorporated by reference for the purpose of describing and disclosing the formulations and methodologies that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication method performed in vitro as compared to its starting amount in a maternal sample.

The term "chromosomal abnormality" refers to any genetic variant for all or part of a chromosome. The genetic variants may include but not be limited to any copy number variant such as duplications or deletions, translocations, inversions, and mutations.

The terms "complementary" or "complementarity" are used in reference to nucleic acid molecules (i.e., a sequence of nucleotides) that are related by base-pairing rules. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100% complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Stringent hybridization conditions will typically include salt concentrations of less than about 1 M, more usually less than about 500 mM and preferably less than about 200 mM. Hybridization temperatures are generally at least about 2° C. to about 6° C. lower than melting temperatures ($T_m$).

The term "correction index" refers to an index that may contain additional nucleotides that allow for identification and correction of amplification, sequencing or other experimental errors including the detection of deletion, substitution, or insertion of one or more bases during sequencing as well as nucleotide changes that may occur outside of sequencing such as oligo synthesis, amplification, and any other aspect of the assay. These correction indices may be stand-alone indices that are separate sequences, or they may be embedded within other indices to assist in confirming accuracy of the experimental techniques used, e.g., a correction index may be a subset of sequences of a locus index or an identification index.

The term "diagnostic tool" as used herein refers to any composition or assay of the invention used in combination as, for example, in a system in order to carry out a diagnostic test or assay on a patient sample.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The term "identification index" refers generally to a series of nucleotides incorporated into a primer region of an amplification process for unique identification of an amplification product of a nucleic acid region. Identification index sequences are preferably 6 or more nucleotides in length. In a preferred aspect, the identification index is long enough to have statistical probability of labeling each molecule with a target sequence uniquely. For example, if there are 3000 copies of a particular target sequence, there are substantially more than 3000 identification indexes such that each copy of a particular target sequence is likely to be labeled with a unique identification index. The identification index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay. The index may be combined with any other index to create one index that provides information for two properties (e.g. sample-identification index, locus-identification index).

The terms "locus" and "loci" as used herein refer to a nucleic acid region of known location in a genome.

The term "locus index" refers generally to a series of nucleotides that correspond to a known locus on a chromosome. Generally, the locus index is long enough to label each known locus region uniquely. For instance, if the method uses 192 known locus regions corresponding to 192 individual sequences associated with the known loci, there are at least 192 unique locus indexes, each uniquely identifying a region indicative of a particular locus on a chromosome. The locus indices used in the methods of the invention may be indicative of different loci on a single chromosome as well as known loci present on different chromosomes within a sample. The locus index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay.

The term "maternal sample" as used herein refers to any sample taken from a pregnant mammal which comprises both fetal and maternal cell free genomic material (e.g., DNA). Preferably, maternal samples for use in the invention are obtained through relatively non-invasive means, e.g., phlebotomy or other standard techniques for extracting peripheral samples from a subject.

The term "melting temperature" or $T_m$ is commonly defined as the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 16.6(\log 10[Na+]) 0.41(\%[G+C]) - 675/n - 1.0$ m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual*, 3rd Ed., Cold Spring Harbor Laboratory Press (2001)). Other references include more sophisticated computations, which take structural as well as sequence characteristics into account for the calculation of $T_m$.

"Microarray" or "array" refers to a solid phase support having a surface, preferably but not exclusively a planar or substantially planar surface, which carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., *Microarrays: A Practical Approach*, IRL Press, Oxford (2000). "Array analysis", "analysis by array" or "analysis by microarray" refers to analysis, such as, e.g., sequence analysis, of one or more biological molecules using a microarray.

The term "mixed sample" as used herein refers to any sample comprising cell free genomic material (e.g., DNA) from two or more cell types of interest. Exemplary mixed samples include a maternal sample (e.g., maternal blood, serum or plasma comprising both maternal and fetal DNA), and a peripherally-derived somatic sample (e.g., blood, serum or plasma comprising different cell types, e.g., hematopoietic cells, mesenchymal cells, and circulating cells from other organ systems). Mixed samples include samples with genomic material from two different sources, which may be sources from a single individual, e.g., normal and atypical somatic cells, or cells that are from two different individuals, e.g., a sample with both maternal and fetal genomic material or a sample from a transplant patient that comprises cells from both the donor and recipient.

By "non-polymorphic", when used with respect to detection of selected nucleic acid regions, is meant a detection of such nucleic acid region, which may contain one or more polymorphisms, but in which the detection is not reliant on detection of the specific polymorphism within the region. Thus a selected nucleic acid region may contain a polymorphism, but detection of the region using the assay system of the invention is based on occurrence of the region rather than the presence or absence of a particular polymorphism in that region.

As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

According to the present invention, a "nucleotide" may be unlabeled or detectably labeled by well known techniques. Fluorescent labels and their attachment to oligonucleotides are described in many reviews, including Haugland, *Handbook of Fluorescent Probes and Research Chemicals,* 9th Ed., Molecular Probes, Inc., Eugene Oreg. (2002); Keller and Manak, *DNA Probes,* 2nd Ed., Stockton Press, New York (1993); Eckstein, Ed., *Oligonucleotides and Analogues: A Practical Approach,* IRL Press, Oxford (1991); Wetmur, *Critical Reviews in Biochemistry and Molecular Biology,* 26:227-259 (1991); and the like. Other methodologies applicable to the invention are disclosed in the following sample of references: Fung et al., U.S. Pat. No. 4,757,141; Hobbs, Jr., et al., U.S. Pat. No. 5,151,507; Cruickshank, U.S. Pat. No. 5,091,519; Menchen et al., U.S. Pat. No. 5,188,934; Begot et al., U.S. Pat. No. 5,366,860; Lee et al., U.S. Pat. No. 5,847,162; Khanna et al., U.S. Pat. No. 4,318,846; Lee et al., U.S. Pat. No. 5,800,996; Lee et al., U.S. Pat. No. 5,066,580: Mathies et al., U.S. Pat. No. 5,688,648; and the like. Labeling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), CASCADE BLUE® (pyrenyloxytrisulfonic acid), OREGON GREEN™ (2',7'-difluorofluorescein), TEXAS RED™ (sulforhodamine 101 acid chloride), Cyanine and 5-(2'-aminoethyl)aminonaphthalene-1-sulfonic acid (EDANS). Specific examples of fluroescently labeled nucleotides include [R6G]dUTP, [TAMRA]dUTP, [R110]dCTP, [R6G]dCTP, [TAMRA] dCTP, [JOE]ddATP, [R6G]ddATP, [FAM]ddCTP, [R110] ddCTP, [TAMRA]ddGTP, [ROX]ddTTP, [dR6G]ddATP, [dR110]ddCTP, [dTAMRA]ddGTP, and [dROX]ddTIP available from Perkin Elmer, Foster City, Calif. FluoroLink DeoxyNucleotides, FluoroLink Cy3-dCTP, FluoroLink Cy5-dCTP, FluoroLink FluorX-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosomee Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, CASCADE BLUE®-7-UTP (pyrenyloxytrisulfonic acid-7-UTP), CASCADE BLUE®-7-dUTP (pyrenyloxytrisulfonic acid-7-dUTP), fluorescein-12-UTP, fluorescein-12-dUTP, OREGON GREEN™ 488-5-dUTP (2',7'-difluorofluorescein-5-dUTP), RHODAMINE GREEN™-5-UTP ((5-{2-[4-(aminomethyl)phenyl]-5-(pyridin-4-yl)-1H-i-5-UTP)), RHODAMINE GREEN®-5-dUTP ((5-{2-[4-(aminomethyl) phenyl]-5-(pyridin-4-yl)-1H-i-5-dUTP)), tetramethylrhodamine-6-UTP, tetramethylrhodamine-6-dUTP, TEXAS RED™-5-UTP (sulforhodamine 101 acid chloride-5-UTP), TEXAS RED™-5-dUTP (sulforhodamine 101 acid chloride-5-dUTP), and TEXAS RED™-12-dUTP (sulforhodamine 101 acid chloride-12-dUTP) available from Molecular Probes, Eugene, Oreg.

The terms "oligonucleotides" or "oligos" as used herein refer to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more. Suitable nucleic acid molecules may be prepared by the phosphoramidite method described by Beaucage and Carruthers (Tetrahedron Lett., 22:1859-1862 (1981)), or by the triester method according to Matteucci, et al. (J. Am. Chem. Soc., 103:3185 (1981)), both incorporated herein by reference, or by other chemical methods such as using a commercial automated oligonucleotide synthesizer.

As used herein the term "polymerase" refers to an enzyme that links individual nucleotides together into a long strand, using another strand as a template. There are two general types of polymerase-DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification methods may be used as an alternative to PCR.

The term "polymorphism" as used herein refers to any genetic changes in a locus that may be indicative of that particular locus, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a nucleic acid region to a capture oligonucleotide for detection of a specific nucleic acid region.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "sample index" refers generally to a series of unique nucleotides (i.e., each sample index is unique to a sample in a multiplexed assay system for analysis of multiple samples). The sample index can thus be used to assist in nucleic acid region identification for multiplexing of different samples in a single reaction vessel, such that each sample can be identified based on its sample index. In a preferred aspect, there is a unique sample index for each sample in a set of samples, and the samples are pooled during sequencing. For example, if twelve samples are pooled into a single sequencing reaction, there are at least twelve unique sample indexes such that each sample is labeled uniquely. The index may be combined with any other index to create one index that provides information for two properties (e.g., sample-identification index, sample-locus index).

The term "selected nucleic acid region" as used herein refers to a nucleic acid region corresponding to an individual chromosome. Such selected nucleic acid regions may be directly isolated and enriched from the sample for detection, e.g., based on hybridization and/or other sequence-based techniques, or they may be amplified using the sample as a template prior to detection of the sequence. Nucleic acids regions for use in the assay systems of the present invention may be selected on the basis of DNA level variation between individuals, based upon specificity for a particular chromosome, based on CG content and/or required amplification conditions of the selected nucleic acid regions, or other characteristics that will be apparent to one skilled in the art upon reading the present disclosure.

The terms "sequencing", "sequence determination" and the like as used herein refers generally to any and all biochemical methods that may be used to determine the order of nucleotide bases in a nucleic acid.

The term "specifically binds", "specific binding" and the like as used herein, when referring to a binding partner (e.g., a nucleic acid probe or primer, antibody, etc.) that results in the generation of a statistically significant positive signal under the designated assay conditions. Typically the interaction will subsequently result in a detectable signal that is at least twice the standard deviation of any signal generated as a result of undesired interactions (background).

The Invention in General

The present invention provides improved methods for identifying copy number variants of particular genomic regions, including complete chromosomes (e.g., aneuploidies), in mixed samples. The detection methods of the invention are not reliant upon the presence or absence of any polymorphic or mutation information, and thus are conceptually agnostic as to the genetic variation that may be present in any chromosomal region under interrogation. These methods are useful for any mixed sample containing cell free genomic material (e.g., DNA) from two or more cell types of interest, e.g., mixed samples comprising maternal and fetal cell free DNA, mixed samples comprising cell free DNA from normal and putatively malignant cells, mixed samples comprising cell free DNA from a transplant donor and recipient, and the like.

The assay methods of the invention provide a selected enrichment of nucleic acid regions from chromosomes of interest and/or reference chromosomes for copy number variant detection. A distinct advantage of the invention is that the enriched selected nucleic acid regions can be further analyzed using a variety of detection and quantification techniques, including but not limited to hybridization techniques, digital PCR and high throughput sequencing determination techniques. Selection probes can be designed against any number of nucleic acid regions for any chromosome. Although amplification prior to the identification and quantification of the selection nucleic acids regions is not mandatory, limited amplification prior to detection is preferred.

The present invention provides an improved system over more random techniques such as massively parallel sequencing, shotgun sequencing, and the use of random digital PCR which have been used by others to detect copy number variations in mixed samples such as maternal blood. These aforementioned approaches rely upon sequencing of all or a statistically significant population of DNA fragments in a sample, followed by mapping of these fragments or otherwise associating the fragments to their appropriate chromosomes. The identified fragments are then compared against each other or against some other reference (e.g. normal chromosomal makeup) to determine copy number variation of particular chromosomes. These methods are inherently inefficient from the present invention, as the primary chromosomes of interest only constitute a minority of data that is generated from the detection of such DNA fragments in the mixed samples.

Techniques that are dependent upon a very broad sampling of DNA in a sample are providing a very broad coverage of the DNA analyzed, but in fact are sampling the DNA contained within a sample on a 1× or less basis (i.e., subsampling). In contrast, the selective amplification and/or enrichment used in the present assays are specifically designed to provide depth of coverage of particular nucleic acids of interest, and provide a "super-sampling" of such selected regions with an average sequence coverage of preferably 2× or more, more preferably sequence coverage of 100× of more, even more preferably sequence coverage of 1000× or more of the selected nucleic acids present in the initial mixed sample.

The methods of the invention provide a more efficient and economical use of data, and the substantial majority of sequences analyzed following sample amplification result in affirmative information about the presence of a particular chromosome in the sample. Thus, unlike techniques relying on massively parallel sequencing or random digital "counting" of chromosome regions and subsequent identification of relevant data from such counts, the assay system of the invention provides a much more efficient use of data collection than the random approaches taught by others in the art.

The sequences analyzed using the assay system of the present invention are enriched and/or amplified representative sequences selected from various regions of the chromosomes of interest to determine the relative quantity of the chromosomes in the mixed sample, and the substantial majority of sequences analyzed are informative of the presence of a region on a chromosome of interest and/or a reference chromosome. These techniques do not require the analysis of large numbers of sequences which are not from the chromosomes of interest and which do not provide information on the relative quantity of the chromosomes of interest.

Detecting Chromosomal Aneuploidies

The present invention provides methods for identifying fetal chromosomal aneuploidies in maternal samples comprising both maternal and fetal DNA. This can be performed using enrichment and/or amplification methods for identification of nucleic acid regions corresponding to specific chromosomes of interest and/or reference chromosomes in the maternal sample.

The assay systems utilize nucleic acid probes designed to identify, and preferably to isolate, selected nucleic acids regions in a mixed sample that correspond to individual chromosomes of interest and, in certain aspects, to reference chromosomes that are used to determine the presence or absence of aneuploidy in a mixed sample. These probes are specifically designed to hybridize to a selected nucleic acid region of a particular chromosome, and thus quantification of the nucleic acid regions in a mixed sample using these probes is indicative of the copy number of a particular chromosome in the mixed sample.

In preferred aspects, the assay systems of the invention employ one or more selective amplification or enrichment steps (e.g., using one or more primers that specifically hybridize to a selected nucleic acid region) to enhance the DNA content of a sample and/or to provide improved mechanisms for isolating, amplifying or analyzing the selected nucleic acid regions. This is in direct contrast to the random amplification approach used by others employing, e.g., massively parallel sequencing, as such amplification techniques generally involve random amplification of all or a substantial portion of the genome.

In a general aspect, the user of the invention analyzes multiple target sequences on different chromosomes and determines the frequency or amount of the target sequences of the chromosomes together. When multiple target sequences are analyzed on chromosomes, a preferred embodiment is to amplify all of the target sequences for each sample in one reaction vessel. The frequency or amount of the multiple target sequences on the different chromosomes is then compared to determine whether a chromosomal abnormality exists.

In one aspect, the user of the invention analyzes multiple target sequences on multiple chromosomes and averages the frequency of the target sequences on the multiple chromosomes together. Normalization or standardization of the frequencies can be performed for one or more target sequences.

In another aspect, the user of the invention sums the frequencies of the target sequences on each chromosome and then compares the sum of the target sequences on one chromosome against another chromosome to determine whether a chromosomal abnormality exists. In another aspect, one analyzes subsets of target sequences on each chromosome to determine whether a chromosomal abnormality exists. The comparison can be made either within the same or different chromosomes.

In certain aspects, the data used to determine the frequency of the target sequences may exclude outlier data that appear to be due to experimental error, or that have elevated or depressed levels based on an idiopathic genetic bias within a particular sample. In one example, the data used for summation may exclude DNA regions with a particularly elevated frequency in one or more samples. In another example, the data used for summation may exclude target sequences that are found in a particularly low abundance in one or more samples.

In another aspect subsets of loci can be chosen randomly but with sufficient numbers of loci to yield a statistically significant result in determining whether a chromosomal abnormality exists. Multiple analyses of different subsets of loci can be performed within a mixed sample to yield more statistical power. For example, if there are 100 selected regions for chromosome 21 and 100 selected regions for chromosome 18, a series of analyses could be performed that evaluate fewer than 100 regions for each of the chromosomes. In this example, target sequences are not being selectively excluded.

The quantity of different nucleic acids detectable on certain chromosomes may vary depending upon a number of factors, including general representation of fetal loci in maternal samples, degradation rates of the different nucleic acids representing fetal loci in maternal samples, sample preparation methods, and the like. Thus, in another aspect, the quantity of particular loci on a chromosome are summed to determine the loci quantity for different chromosomes in the sample. The loci frequency are summed for a particular chromosome, and the sum of the loci are used to determine aneuploidy. This aspect of the invention sums the frequencies of the individual loci on each chromosome and then compares the sum of the loci on one chromosome against another chromosome to determine whether a chromosomal abnormality exists.

The nucleic acids analyzed using the assay systems of the invention are preferably selectively amplified and optionally isolated from the mixed sample using primers specific to the nucleic acid region of interest (e.g., to a locus of interest in a maternal sample). The primers for such selective amplification designed to isolate regions may be chosen for various reasons, but are preferably designed to 1) efficiently amplify a region from the chromosome of interest; 2) have a predictable range of expression from maternal and/or fetal sources in different maternal samples; 3) be distinctive to the particular chromosome, i.e., not amplify homologous regions on other chromosomes. The following are exemplary techniques that may be employed in the assay system or the invention.

Selected Amplification

Numerous selective amplification methods can be used to provide the amplified nucleic acids that are analyzed in the assay systems of the invention, and such methods are preferably used to increase the copy numbers of a nucleic acid region of interest in a mixed sample in a manner that allows preservation of information concerning the initial content of the nucleic acid region in the mixed sample. Although not all combinations of amplification and analysis are described herein in detail, it is well within the skill of those in the art to utilize different amplification methods and/or analytic tools to isolate and/or analyze the nucleic acids of region consistent with this specification, and such variations will be apparent to one skilled in the art upon reading the present disclosure.

Such amplification methods include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. Other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In some aspects DNA is amplified by multiplex locus-specific PCR. In a preferred aspect the DNA is amplified using adaptor-ligation and single primer PCR. Other available methods of amplification, such as balanced PCR (Makrigiorgos, et al. (2002), Nat Biotechnol, Vol. 20, pp. 936-9) and isothermal amplification methods such as nucleic acid sequence based amplification (NASBA) and self-sustained sequence replication (Guatelli et al., Proc. Natl. Acad. Sci. USA 87: 1874, 1990). Based on such methodologies, a person skilled in the art can readily design primers in any suitable regions 5' and 3' to a nucleic acid region of interest. Such primers may be used to amplify DNA of any length so long that it contains the nucleic acid region of interest in its sequence.

The length of an amplified selected nucleic acid from a genomic region of interest is generally long enough to provide enough sequence information to distinguish it from other nucleic acids that are amplified and/or selected. Generally, an amplified nucleic acid is at least about 16 nucleotides in length, and more typically, an amplified nucleic acid is at least about 20 nucleotides in length. In a preferred aspect of the invention, an amplified nucleic acid is at least about 30 nucleotides in length. In a more preferred aspect of the invention, an amplified nucleic acid is at least about 32, 40, 45, 50, or 60 nucleotides in length. In other aspects of the invention, an amplified nucleic acid can be about 100, 150 or up to 200 in length.

In certain aspects, the selected amplification comprises an initial linear amplification step. This can be particularly useful if the starting amount of DNA is quite limited, e.g., where the cell-free DNA in a sample is available in limited quantities. This mechanism increases the amount of DNA molecules that are representative of the original DNA content, and help to reduce sampling error where accurate quantification of the DNA or a fraction of the DNA (e.g., fetal DNA contribution in a maternal sample) is needed.

Thus, in one aspect, a limited number of cycles of sequence-specific linear amplification are performed on the starting maternal sample comprising cell free DNA. The number of cycles is generally less than that used for a typical PCR amplification, e.g., 5-30 cycles or fewer. Primers or probes may be designed to amplify specific genomic segments or regions. The primers or probes may be modified with an end label at the 5' end (e.g. with biotin) or elsewhere along the primer or probe such that the amplification products could be purified or attached to a solid substrate (e.g., bead or array) for further isolation or analysis. In a preferred aspect, the primers are multiplexed such that a single reaction yields multiple DNA fragments from different regions. Amplification products from the linear amplification could then be further amplified with standard PCR methods or with additional linear amplification.

For example, cell free DNA can be isolated from blood, plasma, or serum from a pregnant woman, and incubated with primers against a set number of nucleic acid regions that correspond to chromosomes of interest. Preferably, the number of primers used for initial linear amplification will be 12 or more, more preferably 24 or more, more preferably 36 or more, even more preferably 48 or more, and even more preferably 96 or more. Each of the primers corresponds to a single nucleic acid region, and is optionally tagged for identification and/or isolation. A limited number of cycles, preferably 10 or fewer, are performed with linear amplification. The amplification products are subsequently isolated, e.g., when the primers are linked to a biotin molecule the amplification products can be isolated via binding to avidin or streptavidin on a solid substrate. The products are then subjected to further biochemical processes such as further amplification with other primers and/or detection techniques such as sequence determination and hybridization.

Efficiencies of linear amplification may vary between sites and between cycles so that in certain systems normalization may be used to ensure that the products from the linear amplification are representative of the nucleic acid content starting material. One practicing the assay system of the invention can utilize information from various samples to determine variation in nucleic acid levels, including variation in different nucleic acid regions in individual samples and/or between the same nucleic acid regions in different samples following the limited initial linear amplification. Such information can be used in normalization to prevent skewing of initial levels of DNA content.

Universal Amplification

In preferred aspects of the invention, the selectively amplified nucleic acid regions are preferably amplified following selective amplification or enrichment, either prior to or during the nucleic acid region detection techniques. In another aspect of the invention, nucleic acid regions are selectively amplified during the nucleic acid region detection technique without any prior amplification. In a multiplexed assay system, this is preferably done through universal amplification of the various nucleic acid regions to be analyzed using the assay systems of the invention. Universal primer sequences are added to the selectively amplified nucleic acid regions so that they may be further amplified in a single universal amplification reaction. These universal primer sequences may be added to the nucleic acids regions during the selective amplification process, i.e., the primers for selective amplification have universal primer sequences that flank a locus. Alternatively, adapters comprising universal amplification sequences can be added to the ends of the selected nucleic acids as adapters following amplification and isolation of the selected nucleic acids from the mixed sample.

In one exemplary aspect, nucleic acids are initially amplified from a maternal sample using primers complementary to selected regions of the chromosomes of interest, followed by a universal amplification step to increase the number of nucleic acid regions for analysis. This introduction of primer regions to the initial amplification products from a maternal sample allows a subsequent controlled universal amplification of all or a portion of selected nucleic acids prior to or during analysis, e.g. sequence determination.

Bias and variability can be introduced during DNA amplification, such as that seen during polymerase chain reaction (PCR). In cases where an amplification reaction is multiplexed, there is the potential that loci will amplify at different rates or efficiency. Part of this may be due to the variety of primers in a multiplex reaction with some having better efficiency (i.e. hybridization) than others, or some working better in specific experimental conditions due to the base composition. Each set of primers for a given locus may behave differently based on sequence context of the primer and template DNA, buffer conditions, and other conditions. A universal DNA amplification for a multiplexed assay system will generally introduce less bias and variability.

Accordingly, in a preferred aspect, a small number (e.g., 1-10, preferably 3-5) of cycles of selected amplification or nucleic acid enrichment in a multiplexed mixture reaction are performed, followed by universal amplification using introduced universal primers. The number of cycles using universal primers will vary, but will preferably be at least 10 cycles, more preferably at least 5 cycles, even more preferably 20 cycles or more. By moving to universal amplification following a lower number of amplification cycles, the bias of having certain loci amplify at greater rates than others is reduced.

Optionally, the assay system will include a step between the selected amplification and universal amplification to remove any excess nucleic acids that are not specifically amplified in the selected amplification.

The whole product or an aliquot of the product from the selected amplification may be used for the universal amplification. The same or different conditions (e.g., polymerase, buffers, and the like) may be used in the amplification steps, e.g., to ensure that bias and variability is not inadvertently introduced due to experimental conditions. In addition, variations in primer concentrations may be used to effectively limit the number of sequence specific amplification cycles.

In certain aspects, the universal primer regions of the primers or adapters used in the assay system are designed to be compatible with conventional multiplexed assay methods that utilize general priming mechanisms to analyze large numbers of nucleic acids simultaneously in one reaction in one vessel. Such "universal" priming methods allow for efficient, high volume analysis of the quantity of nucleic acid regions present in a mixed sample, and allow for comprehensive quantification of the presence of nucleic acid regions within such a mixed sample for the determination of aneuploidy.

Examples of such assay methods include, but are not limited to, multiplexing methods used to amplify and/or genotype a variety of samples simultaneously, such as those described in Oliphant et al., U.S. Pat. No. 7,582,420.

Some aspects utilize coupled reactions for multiplex detection of nucleic acid sequences where oligonucleotides from an early phase of each process contain sequences which may be used by oligonucleotides from a later phase of the process. Exemplary processes for amplifying and/or detecting nucleic acids in samples can be used, alone or in combination, including but not limited to the methods described below, each of which are incorporated by reference in their entirety.

In certain aspects, the assay system of the invention utilizes one of the following combined selective and universal amplification techniques: (1) LDR coupled to PCR; (2) primary PCR coupled to secondary PCR coupled to LDR; and (3) primary PCR coupled to secondary PCR. Each of these aspects of the invention has particular applicability in detecting certain nucleic acid characteristics. However, each requires the use of coupled reactions for multiplex detection of nucleic acid sequence differences where oligonucleotides from an early phase of each process contain sequences which may be used by oligonucleotides from a later phase of the process.

Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe the use of the ligase detection reaction with detection reaction ("LDR") coupled with polymerase chain reaction ("PCR") for nucleic acid detection.

Barany et al., U.S. Pat. Nos. 7,556,924 and 6,858,412, describe the use of padlock probes (also called "precircle probes" or "multi-inversion probes") with coupled ligase detection reaction ("LDR") and polymerase chain reaction ("PCR") for nucleic acid detection.

Barany et al., U.S. Pat. Nos. 7,807,431, 7,709,201, and 7,198, 814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping, including Ronaghi et al., U.S. Pat. No. 7,622,281 describes amplification techniques for labeling and amplifying a nucleic acid using an adapter comprising a unique primer and a barcode.

In addition to the various amplification techniques, numerous methods of sequence determination are compatible with the assay systems of the inventions. Preferably, such methods include "next generation" methods of sequencing. Exemplary methods for sequence determination include, but are not limited to, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Alternatively, nucleic acid regions of interest can be selected and/or identified using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al. Molecular Cloning: A Laboratory Manual (2.sup.nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Use of Indices in the Assay Systems of the Invention

In certain aspects, all or a portion of the sequences of the nucleic acids of interest are directly detected using the described techniques, e.g., sequence determination or hybridization. In certain aspects, however, the nucleic acids of interest are associated with one or more indices that are identifying for a selected nucleic acid region or a particular sample being analyzed. The detection of the one or more indices can serve as a surrogate detection mechanism of the selected nucleic acid region, or as confirmation of the presence of a particular selected nucleic acid region if both the sequence of the index and the sequence of the nucleic acid region itself are determined. These indices are preferably associated with the selected nucleic acids during an amplification step using primers that comprise both the index and sequence regions that specifically hybridize to the nucleic acid region.

In one example, the primers used for amplification of a selected nucleic acid region are designed to provide a locus index between the selected nucleic acid region primer region and a universal amplification region. The locus index is unique for each selected nucleic acid region and representative of a locus on a chromosome of interest or reference chromosome, so that quantification of the locus index in a sample provides quantification data for the locus and the particular chromosome containing the locus.

In another example, the primers used for amplification of a selected nucleic acid region are designed to provide an allele index between the selected nucleic acid region primer region and a universal amplification region. The allele index is unique for particular alleles of a selected nucleic acid region and representative of a locus variation present on a chromosome of interest or reference chromosome, so that quantification of the allele index in a sample provides quantification data for the allele and the summation of the allelic indices for a particular locus provides quantification data for both the locus and the particular chromosome containing the locus.

In another aspect, the primers used for amplification of the selected nucleic acid regions to be analyzed for a mixed sample are designed to provide an identification index between the selected nucleic acid region primer region and a universal amplification region. In such an aspect, a sufficient number of identification indices are present to uniquely identify each selected nucleic acid region in the sample. Each nucleic acid region to be analyzed is associated with a unique identification index, so that the identification index is uniquely associated with the selected nucleic acid region. Quantification of the identification index in a sample provides quantification data for the associated selected nucleic acid region and the chromosome corresponding to the selected nucleic acid region. The identification locus may also be used to detect any amplification bias that occurs downstream of the initial isolation of the selected nucleic acid regions from a sample.

In certain aspects, only the locus index and/or the identification index (if present) are detected and used to quantify the selected nucleic acid regions in a sample. In another aspect, a count of the number of times each locus index occurs with a unique identification index is done to determine the relative frequency of a selected nucleic acid region in a sample.

In some aspects, indices representative of the sample from which a nucleic acid is isolated are used to identify the source of the nucleic acid in a multiplexed assay system. In such aspects, the nucleic acids are uniquely identified with the sample index. Those uniquely identified oligonucleotides may then be combined into a single reaction vessel with nucleic acids from other samples prior to sequencing. The sequencing data is first segregated by each unique sample index prior to determining the frequency of each target locus for each sample and prior to determining whether there is a chromosomal abnormality for each sample. For detection, the sample indices, the locus indices, and the identification indices (if present), are sequenced.

In aspects of the invention using indices, the selective amplification primers are preferably designed so that indices comprising identifying information are coded at one or both ends of the primer. Alternatively, the indices and universal amplification sequences can be added to the selectively amplified nucleic acids following initial amplification.

The indices are non-complementary but unique sequences used within the primer to provide information relevant to the selective nucleic acid region that is isolated and/or amplified using the primer. The advantage of this is that information on the presence and quantity of the selected nucleic acid region can be obtained without the need to determine the actual sequence itself, although in certain aspects it may be desirable to do so. Generally, however, the ability to identify and quantify a selected nucleic acid region through identification of one or more indices will decrease the length of sequencing required as the loci information is captured at the 3' or 5' end of the isolated selected nucleic acid region. Use of indices identification as a surrogate for identification of selected nucleic acid regions may also reduce error since longer sequencing reads are more prone to the introduction or error.

In addition to locus indices, allele indices and identification indices, additional indices can be introduced to primers to assist in the multiplexing of samples. For example, correction indices which identify experimental error (e.g., errors introduced during amplification or sequence determination) can be used to identify potential discrepancies in experimental procedures and/or detection methods in the assay systems. The order and placement of these indices, as well as the length of these indices, can vary, and they can be used in various combinations. The primers used for identification and quantification of a selected nucleic acid region may be associated with regions complementary to the 5' of the selected nucleic acid region, or in certain amplification regimes the indices may be present on one or both of a set of amplification primers which comprise sequences complementary to the sequences of the selected nucleic acid region. The primers can be used to multiplex the analysis of multiple selected nucleic acid regions to be analyzed within a sample, and can be used either in solution or on a solid substrate, e.g., on a microarray or on a bead. These primers may be used for linear replication or amplification, or they may create circular constructs for further analysis.

Variation Minimization within and Between Samples

One challenge with the detection of chromosomal abnormalities in a mixed sample is that often the DNA from the cell type with the putative chromosomal abnormality is present in much lower abundance than the DNA from normal cell type. In the case of a mixed maternal sample containing fetal and maternal cell free DNA, the cell free fetal DNA as a percentage of the total cell free DNA may vary from less than one to forty percent, and most commonly is present at or below twenty percent and frequently at or below ten percent. In the detection of an aneuploidy such as Trisomy 21 (Down Syndrome) in the fetal DNA of such mixed maternal sample, the relative increase in Chromosome 21 is 50% in the fetal DNA and thus as a percentage of the total DNA in a mixed sample where, as an example, the fetal DNA is 5% of the total, the increase in Chromosome 21 as a percentage of the total is 2.5%. If one is to detect this difference robustly through the methods described herein, the variation in the measurement of Chromosome 21 has to be much less than the percent increase of Chromosome 21.

The variation between levels found between samples and/or for nucleic acid regions within a sample may be minimized in a combination of analytical methods, many of which are described in this application. For instance, variation is lessened by using an internal reference in the assay. An example of an internal reference is the use of a chromosome present in a "normal" abundance (e.g., disomy for an autosome) to compare against a chromosome present in putatively abnormal abundance, such as aneuploidy, in the same sample. While the use of one such "normal" chromosome as a reference chromosome may be sufficient, it is also possible to use many normal chromosomes as the internal reference chromosomes to increase the statistical power of the quantification.

One method of using an internal reference is to calculate a ratio of abundance of the putatively abnormal chromosomes to the abundance of the normal chromosomes in a sample, called a chromosomal ratio. In calculating the chromosomal ratio, the abundance or counts of each of the nucleic acid regions for each chromosome are summed together to calculate the total counts for each chromosome. The total counts for one chromosome are then divided by the total counts for a different chromosome to create a chromosomal ratio for those two chromosomes.

Alternatively, a chromosomal ratio for each chromosome may be calculated by first summing the counts of each of the nucleic acid regions for each chromosome, and then dividing the sum for one chromosome by the total sum for two or more chromosomes. Once calculated, the chromosomal ratio is then compared to the average chromosomal ratio from a normal population.

The average may be the mean, median, mode or other average, with or without normalization and exclusion of outlier data. In a preferred aspect, the mean is used. In developing the data set for the chromosomal ratio from the normal population, the normal variation of the measured chromosomes is calculated. This variation may be expressed a number of ways, most typically as the coefficient of variation, or CV. When the chromosomal ratio from the sample is compared to the average chromosomal ratio from a normal population, if the chromosomal ratio for the sample falls statistically outside of the average chromosomal ratio for the normal population, the sample contains an aneuploidy. The criteria for setting the statistical threshold to declare an aneuploidy depend upon the variation in the measurement of the chromosomal ratio and the acceptable false positive and false negative rates for the desired assay. In general, this threshold may be a multiple of the variation observed in the chromosomal ratio. In one example, this threshold is three or more times the variation of the chromosomal ratio. In another example, it is four or more times the variation of the chromosomal ratio. In another example it is five or more times the variation of the chromosomal ratio. In another example it is six or more times the variation of the chromosomal ratio. In the example above, the chromosomal ratio is determined by summing the counts of nucleic acid regions by chromosome. Typically, the same number of nucleic acid regions for each chromosome is used. An alternative method for generating the chromosomal ratio would be to calculate the average counts for the nucleic acid regions for each chromosome. The average may be any estimate of the mean, median or mode, although typically an average is used. The average may be the mean of all counts or some variation such as a trimmed or weighted average. Once the average counts for each chromosome have been calculated, the average counts for each chromosome may be divided by the other to obtain a chromosomal ratio between two chromosomes, the average counts for each chromosome may be divided by the sum of the averages for all measured chromosomes to obtain a chromosomal ratio for each chromosome as described above. As highlighted above, the ability to detect an aneuploidy in a mixed sample where the putative DNA is in low relative abundance depends greatly on the variation in the measurements of different nucleic acid regions in the assay. Numerous analytical methods can be used which reduce this variation and thus improve the sensitivity of this method to detect aneuploidy. One method for reducing variability of the assay is to increase the number of nucleic acid regions used to calculate the abundance of the chromosomes. In general, if the measured variation of a single nucleic acid region of a chromosome is X % and Y different nucleic acid regions are measured on the same chromosome, the variation of the measurement of the chromosomal abundance calculated by summing or averaging the abundance of each nucleic acid region on that chromosome will be approximately X % divided by $Y^{\wedge}/2$. Stated differently, the variation of the measurement of the chromosome abundance would be approximately the average variation of the measurement of each nucleic acid region's abundance divided by the square root of the number of nucleic acid regions.

In a preferred aspect of this invention, the number of nucleic acid regions measured for each chromosome is at least 24. In another preferred aspect of this invention, the number of nucleic acid regions measured for each chromosome is at least 48. In another preferred aspect of this invention, the number of nucleic acid regions measured for each chromosome is at least 100. In another preferred aspect of this invention the number of nucleic acid regions measured for each chromosome is at least 200. There is incremental cost to measuring each nucleic acid region and thus it is important to minimize the number of each nucleic acid region. In a preferred aspect of this invention, the number of nucleic acid regions measured for each chromosome is less than 2000. In a preferred aspect of this invention, the number of nucleic acid regions measured for each chromosome is less than 1000. In a most preferred aspect of this invention, the number of nucleic acid regions measured for each chromosome is at least 48 and less than 1000. In one aspect, following the measurement of abundance for each nucleic acid region, a subset of the nucleic acid regions may be used to determine the presence or absence of aneuploidy. There are many standard methods for choosing the subset of nucleic acid regions. These methods include outlier exclusion, where the nucleic acid regions with detected levels below and/or above a certain percentile are discarded from the analysis. In one aspect, the percentile may be the lowest and highest 5% as measured by abundance. In another aspect, the percentile may be the lowest and highest 10% as measured by abundance. In another aspect, the percentile may be the lowest and highest 25% as measured by abundance.

Another method for choosing the subset of nucleic acid regions include the elimination of regions that fall outside of some statistical limit. For instance, regions that fall outside of one or more standard deviations of the mean abundance may be removed from the analysis. Another method for choosing the subset of nucleic acid regions may be to compare the relative abundance of a nucleic acid region to the expected abundance of the same nucleic acid region in a healthy population and discard any nucleic acid regions that fail the expectation test. To further minimize the variation in the assay, the number of times each nucleic acid region is measured may be increased. As discussed, in contrast to the random methods of detecting aneuploidy where the genome is measured on average less than once, the assay systems of the present invention intentionally measures each nucleic acid region multiple times. In general, when counting events, the variation in the counting is determined by Poisson statistics, and the counting variation is typically equal to one divided by the square root of the number of counts. In a preferred aspect of the invention, the nucleic acid regions are each measured on average at least 100 times. In a preferred aspect to the invention, the nucleic acid regions are each measured on average at least 500 times. In a preferred aspect to the invention, the nucleic acid regions are each measured on average at least 1000 times. In a preferred aspect to the invention, the nucleic acid regions are each measured on average at least 2000 times. In a preferred aspect to the invention, the nucleic acid regions are each measured on average at least 5000 times.

In another aspect, subsets of loci can be chosen randomly but with sufficient numbers of loci to yield a statistically significant result in determining whether a chromosomal abnormality exists. Multiple analyses of different subsets of loci can be performed within a mixed sample to yield more statistical power. In this example, it may or may not be necessary to remove or eliminate any loci prior to the random analysis. For example, if there are 100 selected regions for chromosome 21 and 100 selected regions for chromosome 18, a series of analyses could be performed that evaluate fewer than 100 regions for each of the chromosomes.

In addition to the methods above for reducing variation in the assay, other analytical techniques, many of which are described earlier in this application, may be used in combination. In general, the variation in the assay may be reduced when all of the nucleic acid regions for each sample are interrogated in a single reaction in a single vessel. Similarly, the variation in the assay may be reduced when a universal amplification system is used. Furthermore, the variation of the assay may be reduced when the number of cycles of amplification is limited.

Detection of Genetic Mutations

In certain aspects, the assay system of the invention detects both fetal aneuploidies and specific genetic alterations in specific loci of interest. Such additional genetic alterations include, but are not limited to, deletion mutations, insertion mutations, copy number polymorphisms, copy number variants, chromosome 22q11 deletion syndrome, 11 q deletion syndrome on chromosome 11, 8p deletion syndrome on chromosome 8, and the like. Generally, at least two target nucleic acid sequences present on the same or separate chromosomes are analyzed, and at least one of the target sequences is associated with the fetal allelic abnormality. The sequences of the two target sequences and number of copies of the two target sequences are then compared to determine whether the chromosomal abnormality is present, and if so, the nature of the abnormality.

While much of the description contained herein describes detecting aneuploidy by counting the abundance of nucleic acid regions on one or more putative aneuploid chromosomes and the abundance of nucleic acid regions on one or more normal chromosomes, the same techniques may be used to detect copy number variations where such copy number variation occurs on only a portion of a chromosome. In this detection of the copy number variations, multiple nucleic acid regions within the putative copy number variation location are compared to multiple nucleic acid regions outside of the putative copy number variation location. Other aspects of the invention described for aneuploidy may then be used for the detection of copy number variation. For instance, one may detect a chromosome 22q11 deletion syndrome in a fetus in a mixed maternal sample by selecting two or more nucleic regions within the 22q11 deletion and two or more nucleic acid regions outside of the 22q11 deletion. The nucleic acid regions outside of the 22q11 deletion may be on another region of Chromosome 22 or may be on a completely different chromosome. The abundance of each nucleic acid regions is determined by the methods described in this application.

In some aspects a universal amplification may be used for amplifying the nucleic acid regions. In some aspects, the nucleic acid regions for each sample are assayed in a single reaction in a single vessel. In some aspects, at least 24 nucleic acid regions may be used within the deletion and at least 24 nucleic acid regions may be used outside of the deletion. In another aspect at least 48 nucleic acid regions may be used within the deletion and at least 48 nucleic acid regions may be used outside of the deletion. The nucleic acid regions within the deletion are then summed as are the nucleic acid regions outside of the deletion. These sums are then compared to each other to determine the presence or absence of a deletion. Optionally, the sums are put into a ratio and that ratio may be compared to an average ratio created from a normal population. When the ratio for a sample falls statistically outside of an expected ratio, the deletion is detected. The threshold for the detection of a deletion may be four or more times the variation calculated in the normal population.

Use of Other Fetal Detection Methods

In certain aspects of the invention, the methods of the invention can be used in conjunction with detection of other known risk factors (e.g., maternal age, family history, maternal or paternal genetic information) and/or means for detecting fetal abnormalities, and preferably with other relatively non-invasive diagnostic mechanisms of fetal abnormalities (e.g., measurements of one or more biochemical markers in a maternal sample and/or measurements or structural detection from an ultrasound scan). The combined use of these risk factors and diagnostic mechanisms with the methods of the invention can provide an improved risk determination of fetal abnormality, and in particular the presence or absence of a known genetic mutation such as a trisomy.

Thus, in some preferred aspects the results obtained in the assay systems of the invention are combined with the results from biochemical detection of risk factors, ultrasound detection of risk factors, or other risk determinants of fetal abnormalities.

In some specific aspects, the results obtained in the assay systems of the invention are combined with detection of biochemical markers associated with an increased risk of fetal abnormality. The biochemical markers can be determined based on a sample comprising maternal blood, serum, plasma or urine. Such biochemical markers include but are not limited to: free Beta hCG, pregnancy-associated plasma protein A (PAPP-A), maternal blood alpha-fetoprotein, maternal blood hCG, maternal blood unconjugated estriol, maternal blood dimeric inhibin A, maternal urine total estriol, maternal urine beta core fragment, maternal urine hyperglycosylated hCG, maternal blood hyperglycosylated hCG, and inhibin A (preferably dimeric inhibin A). In some aspects, the additional assessment mechanism is multi-marker analysis, such as that described in Orlandi et al., U.S. Pat. No. 7,315,787 or Wald et al. U.S. Pat. No. 6,573,103. Detection of presence and/or levels of these and other markers can be combined with the results from assay systems of the invention to provide a final result to the patient.

In other specific aspects, the results obtained in the assay systems of the invention are combined with the results obtained from ultrasound images, including but are not limited to: nuchal translucency (NT) thickness or edema, nuchal fold thickness, abnormality of the venous system (including the ductus venosus, the portal and hepatic veins and inferior vena cava), absent or hypoplastic nasal bone, femur length, humerus length, hyperechogenic bowel, renal pyelectasis, echogenic foci in the heart, fetal heart rate, and certain cardiac abnormalities. In specific aspects, the additional assessment of fetal abnormality is performed though shape analysis, such as described in U.S. Pat. Nos. 7,780,600 and 7,244,233. In a specific aspect, the additional assessment is based on the determination of landmarks based on images, as described in U.S. Pat. No. 7,343,190. Detection of these and other physical parameters can be combined with the results from assay systems of the invention to provide a final result to the patient.

Most screening markers and physical characteristics are known to vary with gestational age. To take account of this variation each marker level may be expressed as a multiple of the median level (MoM) for unaffected pregnancies of the same gestational age. Especially, for markers derived from ultrasound scans, crown-rump length (CRL) or biparietal diameter (BPD) measurement are alternative measures of gestational age. MoMs may be adjusted in a known way to take account of factors which are known to affect marker levels, such as maternal weight, ethnic group, diabetic status and the number of fetuses carried.

Use of the above techniques can be performed at a single stage of pregnancy or obtained sequentially at two or more different stages of pregnancy. These marker levels can also be interpreted in combination with variables maternal such as maternal age, weight, ethnicity, etc. to derive a risk estimate. The estimation of risk is conducted using standard statistical techniques. For example, known methods are described in Wald N J et al., *BMJ* (1992); 305(6850):391-4; Wald N J et al (1988) *BMJ* 297:883-887 and in Royston P, Thompson S G Stat Med. (1992) 11(2):257-68.

Detection of Maternal Carrier Status

The assay systems of the present invention are useful not only in determining aneuploidy and other genetic risk factors as they pertain to a fetus, but also to determine the genetic status of the mother at the sites interrogated in the assay system. By detecting certain selected nucleic acid regions that comprise alleles that may contain genetic alterations associated with heritable diseases and disorders, maternal contribution can be detected as well as detecting any genetic alterations that may directly affect the fetus. The assay systems of the invention can thus be used for determining the carrier status of the mother and/or the fetus by detecting genetic alterations within the maternal and/or fetal contribution of the cell free DNA in a maternal sample.

Determining the carrier status of a pregnant female may thus be of value in both the present pregnancy as well as any future pregnancies, as it is predictive of the statistical likelihood that a fetus will inherit the genetic mutation. The American College of Medical Genetics (ACMG) recommends carrier screening by genetic testing for all prospective parents for a number of Mendelian diseases, and the list of diseases that ACMG recommends testing is continually expanding as a function of new discoveries related to genetic diseases. Estimates of genetic load indicate that every human carries approximately 8 to 30 deleterious recessive alleles.

Presently, screening of prospective parents for carrier status of a genetic anomaly (e.g., a point mutation, a translocation, or other genetic alteration associated with one or more disorders) is selective based on relative risk factors, e.g., due to race, ethnicity, family history or other factors that places individuals at increased risk for particular conditions. The assay systems of the invention allow universal testing for a wide variety of genetic conditions for individuals of any ancestry as a matter of course in determining the genetic status of the fetus.

For example, in certain assay systems in which the maternal sample is subjected to interrogation for particular point mutations, indels, and the like associated with disease, the mother's carrier status for such genetic alterations can be determined at the same time the fetal DNA in the maternal sample is interrogated. The ratios of the numbers of mutations detected will allow determination of an affected fetus, a fetus carrying a disease allele, and a mother's carrier status. In some circumstances, the paternal carrier status may be determined as well, e.g., when the fetus is affected with a homozygous autosomal recessive disorder or an autosomal dominant disorder for which the mother is not a carrier. A heterozygous carrier will display the genetic alteration in approximately 50% of the interrogated alleles containing the genetic alteration.

In specific aspects, the mother's carrier status can be determined for mutations associated with autosomal recessive disorders or other clinically relevant SNPs. The mother's carrier status can be determined by the ratio of alleles that comprise the mutation, which will comprise 50% of the maternally derived cell free DNA in a maternal sample. So, for example, when a maternal sample comprises 90% maternally derived DNA and 10% fetal DNA, the 50% of the maternally derived DNA would be 45% of the total DNA in a maternal sample.

Examples of mutations and SNPs that can be detected include but are not limited to those found in a database of genetic variants maintained by the US National Institutes of Health. See Bhagwat M, Curr Protoc Bioinformatics. 2010 December; Chapter 1:Unit 1.19; Phillips C, Mol Biotechnol. 2007 January; 35(1):65-97. The curated records in dbSNP contain information that describes the sequence and location of genetic variants, and where available the frequency of alleles of those variants in different populations.

In other aspects, the mother's carrier status can be determined for mutations associated with autosomal dominant disorders, and in particular autosomal dominant alleles associated with diseases or disorders with an onset following reproductive age. In some aspects, the mother's carrier status can be determined for true autosomal dominant diseases such as, e.g., Huntington's disease. In other specific aspects, the mother's carrier status can be determined for mutations and/or SNPs associated with a predisposition for developing an adult disease or disorder, such as mutations in the BRCA1 and BRCA2 genes for breast and ovarian cancers. In yet other specific aspects, the mother's carrier status can be determined for mutations and/or SNPs associated with a poor prognosis in a disorder, e.g., the apoE4 allele of the apoE gene which is associated with an increased risk for and poor prognosis in Alzheimer's disease.

In particular aspects, the mother's carrier status can be determined for X-linked disorders. Carrier females who have only one copy of the mutation do not usually express the phenotype, although differences in X chromosome inactivation can lead to varying degrees of clinical expression in carrier females since some cells will express one X allele and some will express the other. The current estimate of sequenced X-linked genes is 499 and the total including vaguely defined traits is 983. See, e.g., the OMIM database, Johns Hopkins University. Such disorders include, but are not limited to, Hemophilia A, Hemophilia B, Duchenne muscular dystrophy, Becker's muscular dystrophy, Red-Green color blindness, X-linked ichthyosis, X-linked agammaglobulinemia (XLA); Glucose-6-phosphate dehydrogenase deficiency, Adrenoleukodystrophy, Alport syndrome; Androgen insensitivity syndrome, Barth syndrome; Centronuclear myopathy, Charcot-Marie-Tooth disease (CMTX2-3), Coffin-Lowry syndrome, Fabry disease, Hunter's Syndrome, Hypohidrotic ectodermal dysplasia, Kabuki syndrome, Kennedy disease, Lesch-Nyhan syndrome, Lowe Syndrome, Menkes disease, Nonsyndromic deafness, X-linked nonsyndromic deafness, Norrie disease, Occipital horn syndrome, Ornithine transcarbamylase deficiency, Siderius X-linked mental retardation syndrome (caused by mutations in the histone demethylase PHF8), Simpson-Golabi-Behmel syndrome; Spinal muscular atrophy (caused by a UBE1 gene mutation), Wiskott-Aldrich syndrome, X-linked Severe Combined Immunodeficiency (SCID), and X-linked sideroblastic anemia.

In yet other specific aspects, the mother's carrier status can be determined for chromosomal rearrangements such as translocations, duplications, or deletions. For example, the chromosomal translocations that may be detected in the mother include reciprocal translocations (also known as non-Robertsonian) and Robertsonian. This may be particularly helpful if the mother has a balanced translocation (in an even exchange of material in the mother with no genetic information extra or missing, and ideally full functionality) that may result in an unbalanced translocation (where the exchange of chromosome material is unequal resulting in extra or missing genes) in the fetus. In another example, chromosomal deletions such as the 22q11.2 deletion syndrome (which results in DiGeorge syndrome) can be detected.

In a preferred aspect, the mother's carrier status is determined in a maternal sample at the same time as fetal aneuploidy detection is performed on the same maternal sample. In a preferred aspect the analysis of maternal carrier status and fetal aneuploidy detection is performed at the same time in the same vessel. In a preferred aspect the analysis of maternal carrier status and fetal aneuploidy detection is performed using a highly multiplexed assay format such as disclosed in co-pending application U.S. Ser. No. 13/013,732, Barany et al, Oliphant et al or Willis et al. When the maternal carrier status is performed with fetal aneuploidy detection, maternal alleles are identified separate from paternally derived alleles in the fetus by looking for allele frequencies greater than 25%. The advantages of combining maternal carrier screening with aneuploidy detection include convenience, since only one blood draw is necessary, and cost, since the incremental costs of adding additional tests is much less than testing conditions separately.

Detection of Other Agents or Risk Factors in Mixed Sample

Given the multiplexed nature of the assay systems of the invention, in certain aspects it may be beneficial to utilize the assay to detect other nucleic acids that could pose a risk to the health of the subject(s) or otherwise impact on clinical decisions about the treatment or prognostic outcome for a subject. Such nucleic acids could include but are not limited to indicators of disease or risk such as maternal alleles, polymorphisms, or somatic mutations known to present a risk for maternal or fetal health. Such indicators include, but are not limited to, genes associated with Rh status; mutations or polymorphisms associated with diseases such as diabetes, hyperlipidemia, hypercholesterolemia, blood disorders such as sickle cell anemia, hemophilia or thalassemia, cardiac conditions, etc.; exogenous nucleic acids associated with active or latent infections; somatic mutations or copy number variations associated with autoimmune disorders or malignancies (e.g., breast cancer), or any other health issue that may impact on the subject, and in particular on the clinical options that may be available in the treatment and/or prevention of health risks in a subject based on the outcome of the assay results.

Accordingly, as the preferred assay systems of the invention are highly multiplexed and able to interrogate hundreds or even thousands of nucleic acids within a mixed sample, in certain aspects it is desirable to interrogate the sample for nucleic acid markers within the mixed sample, e.g., nucleic acids associated with genetic risk or that identify the presence or absence of infectious organisms. Thus, in certain aspects, the assay systems provide detection of such nucleic acids in conjunction with the detection of nucleic acids for copy number determination within a mixed sample.

For example, in certain mixed samples of interest, including maternal samples, samples from subjects with autoimmune disease, and samples from patients undergoing chemotherapy, the immune suppression of the subject may increase the risk for the disease due to changes in the subject's immune system. Detection of exogenous agents in a mixed sample may be indicative of exposure to and infection by an infectious agent, and this finding have an impact on patient care or management of an infectious disease for which a subject tests positively for such infectious agent.

Specifically, changes in immunity and physiology during pregnancy may make pregnant women more susceptible to or more severely affected by infectious diseases. In fact, pregnancy itself may be a risk factor for acquiring certain infectious diseases, such as toxoplasmosis, Hansen disease, and listeriosis. In addition, for pregnant women or subjects with suppressed immune systems, certain infectious diseases such as influenza and varicella may have a more severe clinical course, increased complication rate, and higher case-fatality rate. Identification of infectious disease agents may therefore allow better treatment for maternal disease during pregnancy, leading to a better overall outcome for both mother and fetus.

In addition, certain infectious agents can be passed to the fetus via vertical transmission, i.e. spread of infections from mother to baby. These infections may occur while the fetus is still in the uterus, during labor and delivery, or after delivery (such as while breastfeeding).

Thus, is some preferred aspects, the assay system may include detection of exogenous sequences, e.g., sequences from infectious organisms that may have an adverse effect on the health and/or viability of the fetus or infant, in order to protect maternal, fetal, and or infant health.

Exemplary infections which can be spread via vertical transmission, and which can be tested for using the assay methods of the invention, include but are not limited to congenital infections, perinatal infections and postnatal infections.

Congenital infections are passed in utero by crossing the placenta to infect the fetus. Many infectious microbes can cause congenital infections, leading to problems in fetal development or even death. TORCH is an acronym for several of the more common congenital infections. These are: toxoplasmosis, other infections (e.g., syphilis, hepatitis B, Coxsackie virus, Epstein-Barr virus, varicella-zoster virus (chicken pox), and human parvovirus B19 (fifth disease)), rubella, cytomegalovirus (CMV), and herpes simplex virus.

Perinatal infections refer to infections that occur as the baby moves through an infected birth canal or through contamination with fecal matter during delivery. These infections can include, but are not limited to, sexually-transmitted diseases (e.g., gonorrhea, *chlamydia*, herpes simplex virus, human papilloma virus, etc.) CMV, and Group B Streptococci (GBS).

Infections spread from mother to baby following delivery are known as postnatal infections. These infections can be spread during breastfeeding through infectious microbes found in the mother's breast milk. Some examples of postnatal infections are CMV, Human immunodeficiency virus (HIV), Hepatitis C Virus (HCV), and GBS.

In specific aspects, the assay systems of the invention can comprise multiple reactions that interrogate the fetal aneuploidy, detection of other agents or risk factors, and the maternal and/or fetal carrier status in a single reaction. Combining all of these forms of screening requires only one blood draw and is both more efficient and more cost effective, as the incremental costs of adding additional tests is much less than testing conditions separately.

Computer Implementation of the Processes of the Invention

FIG. 1 is a block diagram illustrating an exemplary system environment in which the processes of the present invention may be implemented. The system 10 includes a server 14 and a computer 16, and preferably these are associated with a DNA sequencer 12. The DNA sequencer 12 may be coupled to the server 14 and/or the computer 16 directly or through a network. The computer 16 may be in communication with the server 14 through the same or different network.

The DNA sequencer 12 may be any commercially available instrument that automates the DNA sequencing process for sequence analysis of nucleic acids representative of a nucleic acid in the maternal sample 18. The output of the DNA sequencer 12 may be in the form of multiplexed data sets 20 comprising frequency data for loci and/or samples, and optionally these are distinguishable based on associated indices. In one embodiment, the multiplexed data set 20 may be stored in a database 22 that is accessible by the server 14.

According to the exemplary embodiment, the computer 16 executes a software component 24 that calculates the relative frequencies of the genomic regions and/or chromosomes from a maternal sample 18. In one embodiment, the computer 16 may comprise a personal computer, but the computer 16 may comprise any type of machine that includes at least one processor and memory.

The output of the software component 24 comprises a report 26 with a relative frequency of a genomic region and/or a chromosome and/or results of the comparison of such genomic regions and/or chromosomes. The report 26 may be paper that is printed out, or electronic, which may be displayed on a monitor and/or communicated electronically to users via e-mail, FTP, text messaging, posted on a server, and the like.

Although the processes of the invention are shown as being implemented as software 24, they can also be implemented as a combination of hardware and software. In addition, the software 24 may be implemented as multiple components operating on the same or different computers.

Both the server 14 and the computer 16 may include hardware components of typical computing devices (not shown), including a processor, input devices (e.g., keyboard, pointing device, microphone for voice commands, buttons, touchscreen, etc.), and output devices (e.g., a display device, speakers, and the like). The server 14 and computer 16 may include computer-readable media, e.g., memory and storage devices (e.g., flash memory, hard drive, optical disk drive, magnetic disk drive, and the like) containing computer instructions that implement the functionality disclosed when executed by the processor. The server 14 and the computer 16 may further include wired or wireless network communication interfaces for communication.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, 6.

What is claimed is:

1. A method for simultaneous detection of a presence or absence of a fetal aneuploidy and a carrier status of a maternal allele in a maternal plasma or serum sample, comprising the steps of:
   (a) in a maternal plasma or serum sample comprising maternal and fetal DNA, amplifying two or more selected nucleic acid regions from a first chromosome of interest in the maternal and fetal DNA in the maternal plasma or serum sample with primers complementary to the selected nucleic acid regions from the first chromosome to produce amplified selected maternal and fetal nucleic acid regions in the maternal plasma or serum sample, wherein the amplifying comprises 30 or fewer amplification cycles and the amplified selected maternal and fetal nucleic acid regions from the first chromosome comprise a universal primer binding sequence;
   (b) amplifying two or more selected nucleic acid regions from a second chromosome of interest in the maternal and fetal DNA of the maternal plasma or serum sample with primers complementary to the selected nucleic acid regions from the second chromosome to produce amplified selected maternal and fetal nucleic acid regions in the maternal plasma or serum sample, wherein the amplifying comprises 30 or fewer amplification cycles and the amplified selected maternal and fetal nucleic acid regions from the second chromosome comprise a universal primer binding sequence;
   (c) amplifying one or more selected nucleic acid regions comprising an allele of interest in the maternal and fetal DNA in the maternal plasma or serum sample with primers complementary to the selected nucleic acid regions comprising the allele of interest to produce amplified selected maternal and fetal nucleic acid regions in the maternal plasma or serum sample, wherein the amplifying comprises 30 or fewer amplification cycles the amplified selected maternal and fetal nucleic acid regions comprising the allele of interest comprise a universal primer binding sequence;
   (d) performing universal amplification with universal primers complementary to the universal primer binding sequences, wherein the universal amplification comprises at least 5 cycles, and the amplification steps of (a), (b) and (c) comprise a lower number of amplification cycles than the universal amplification;
   (e) detecting the selected maternal and fetal nucleic acid regions from the first and second chromosomes and allele of interest which were amplified with the universal primers in a single sequencing run, wherein detecting the maternal and fetal nucleic acid sequences of the first and second chromosomes is not reliant on detection of any polymorphism within the selected nucleic acid regions from the first and second chromosomes;
   (f) quantifying a combined relative frequency for each of the amplified selected maternal and fetal nucleic acid regions from the first and second chromosomes of interest;
   (g) comparing the combined relative frequencies of the amplified selected maternal and fetal nucleic acid regions from the first and second chromosomes of interest;
   (h) identifying the presence or absence of a statistical variation in the compared combined relative frequencies of the amplified selected maternal and fetal nucleic acid regions of the first chromosome and the combined relative frequencies of the amplified selected maternal and fetal nucleic acid regions of the second chromosome, and identifying the presence of a fetal aneuploidy when the statistical variation is present and identifying the absence of a fetal aneuploidy when a statistical variation is absent; and
   (i) determining if the amplified selected maternal and fetal nucleic acid regions from the alleles of interest are detected in a frequency indicative of maternal carrier status of the allele.

2. The method of claim 1, wherein the combined relative frequencies of the amplified selected maternal and fetal nucleic acid regions from each of the first and second chromosomes and the allele of interest are individually quantified, and the combined relative frequencies of the individual amplified selected maternal and fetal nucleic acid regions from the first and second chromosomes are compared.

3. The method of claim 1, wherein the amplified selected maternal and fetal nucleic acid regions from the first and second chromosomes and allele of interest are normalized following detection and prior to quantification.

4. The method of claim 1, wherein the amplified selected maternal and fetal nucleic acid regions from the first and second chromosomes and allele of interest are associated with one or more identifying indices.

5. The method of claim 4, wherein the combined relative frequencies of the amplified selected maternal and fetal nucleic acid regions from the first and second chromosomes and allele of interest are determined through identification of the associated one or more identifying indices.

6. The method of claim 1, wherein the amplified selected maternal and fetal nucleic acid regions from the first and second chromosomes and allele of interest are quantified by counting each nucleic acid region an average of at least 500 times.

7. The method of claim 1, wherein the method is performed with maternal plasma.

8. The method of claim 1, wherein the number of amplification cycle using the universal primers is 20 cycles or more.

9. The method of claim 1, wherein the number of amplification cycle using the primers complementary to the selected nucleic acid regions is 5-30.

10. A method for simultaneous detection of a presence or absence of a fetal aneuploidy and a maternal genetic alteration in a locus associated with a heritable disease in a maternal plasma or serum sample comprising the steps of:

(a) in a maternal plasma or serum sample comprising maternal and fetal DNA, amplifying two or more selected nucleic acid regions from a first chromosome of interest in the maternal and fetal DNA in the maternal plasma or serum sample with primers complementary to the selected nucleic acid regions from the first chromosome to produce amplified selected maternal and fetal nucleic acid regions in the maternal plasma or serum sample, wherein the amplifying comprises 30 or fewer amplification cycles, and the amplified selected maternal and fetal nucleic acid regions from the first chromosome comprise a universal primer binding sequence;

(b) amplifying two or more selected nucleic acid regions from a second chromosome of interest in the maternal and fetal DNA in the maternal plasma or serum sample with primers complementary to the selected nucleic acid regions from the second chromosome to produce amplified selected maternal and fetal nucleic acid regions in the maternal plasma or serum sample, wherein the amplifying comprises 30 or fewer amplification cycles and the amplified selected maternal and fetal nucleic acid regions from the second chromosome comprise a universal primer binding sequence;

(c) amplifying one or more selected nucleic acid regions comprising all or part of a locus associated with a heritable disease in the maternal and fetal DNA with primers complementary to the selected nucleic acid regions comprising the allele of interest to produce amplified selected maternal and fetal nucleic acid regions in the maternal plasma or serum sample, wherein the amplifying comprises 30 or fewer amplification cycles and the amplified selected maternal and fetal nucleic acid regions comprising the allele of interest comprise a universal primer binding sequence;

(d) performing universal amplification with universal primers complementary to the universal primer binding sequences, wherein the universal amplification comprises at least 5 cycles, and the amplification steps of (a), (b) and (c) comprise a lower number of amplification cycles than the universal amplification;

(e) detecting the selected maternal and fetal nucleic acid regions from the first and second chromosomes and the locus associated with a heritable trait which were amplified with the universal primers by counting each nucleic acid region an average of at least 100 times in a single sequencing run, wherein detecting the amplified selected maternal and fetal nucleic acid sequences from the first and second chromosomes is not reliant on detection of any polymorphism within the selected nucleic acid regions from the first and second chromosomes;

(f) quantifying a combined relative frequency for each of the amplified selected maternal and fetal nucleic acid regions from the first and second chromosomes of interest;

(g) comparing the combined relative frequency of the amplified selected maternal and fetal nucleic acid regions from the first and second chromosomes of interest;

(h) identifying the presence or absence of a statistical variation in the compared combined relative frequencies of the amplified selected maternal and fetal nucleic acid regions of the first chromosome and the combined relative frequencies of the amplified selected maternal and fetal nucleic acid regions of the second chromosome indicative of the presence or absence of fetal aneuploidy, and identifying the presence of a fetal aneuploidy when the statistical variation is present and identifying the absence of a fetal aneuploidy when a statistical variation is absent; and (i) determining if the amplified selected maternal and fetal nucleic acid regions corresponding to a heritable disease are detected and identifying a presence of the heritable disease in the one or more amplified selected maternal and fetal nucleic acid region comprising all or part of a locus associated with a heritable disease when the amplified selected maternal and fetal nucleic acid regions corresponding to the heritable disease are detected and identifying the absence of the heritable disease in the one or more amplified selected maternal and fetal nucleic acid region comprising all or part of a locus associated with a heritable disease when the amplified selected maternal and fetal nucleic acid regions corresponding to the heritable disease are not detected.

11. The method of claim 10, wherein the amplified selected maternal and fetal nucleic acid regions from the first and second chromosomes and the locus associated with a heritable trait are normalized following detection and prior to quantification.

12. The method of claim 10, wherein the amplified selected maternal and fetal nucleic acid regions from the first and second chromosomes and the locus associated with a heritable trait are associated with one or more identifying indices.

13. The method of claim 12, wherein the combined relative frequency of the amplified selected maternal and fetal nucleic acid regions from the first and second chromosomes and the locus associated with a heritable trait are determined through identification of the associated one or more identifying indices.

14. The method of claim 10, wherein the amplified selected maternal and fetal nucleic acid regions from the first and second chromosomes and the locus associated with a heritable trait are quantified by counting each nucleic acid region an average of at least 500 times.

15. The method of claim 1, wherein the method is performed with maternal plasma.

16. The method of claim 10, wherein the number of amplification cycle using the universal primers is 20 cycles or more.

17. The method of claim 10, wherein the number of amplification cycle using the primers complementary to the selected nucleic acid regions is 5-30.

18. A method for simultaneous detection of a presence or absence of a fetal aneuploidy and a fetal carrier status in a maternal plasma or serum sample, comprising the steps of:

(a) in a maternal plasma or serum sample comprising maternal and fetal DNA, amplifying two or more selected nucleic acid regions from a first chromosome of interest in the maternal and fetal DNA in the maternal plasma or serum sample with primers complementary to the selected nucleic acid regions from the first chromosome to produce amplified selected maternal and fetal nucleic acid regions that in the maternal plasma or serum sample, wherein the amplifying comprises 30 or fewer amplification cycles and the amplified selected maternal and fetal nucleic acid regions from the first chromosome comprise a universal primer binding sequence;

(b) amplifying two or more selected nucleic acid regions from a second chromosome of interest in the maternal and fetal DNA in the maternal plasma or serum sample with primers complementary to the selected nucleic acid regions from the second chromosome to produce amplified selected maternal and fetal nucleic acid regions in the maternal plasma or serum sample, wherein the amplifying comprises 30 or fewer amplification cycles and the amplified selected maternal and fetal nucleic acid regions from the second chromosome comprise a universal primer binding sequence;

(c) amplifying one or more selected nucleic acid regions comprising an allele of interest in the maternal and fetal DNA in the maternal plasma or serum sample with primers complementary to the selected nucleic acid regions comprising the allele of interest to produce amplified selected maternal and fetal nucleic acid regions in the maternal plasma or serum sample, wherein the amplifying comprises 30 or fewer amplification cycles and the amplified selected maternal and fetal nucleic acid regions comprising the allele of interest comprise a universal primer binding sequence;

(d) performing universal amplification with universal primers complementary to the universal primer binding sequences, wherein the universal amplification comprises at least 5 cycles, and the amplification steps of (a), (b) and (c) comprise a lower number of amplification cycles than the universal amplification;

(e) detecting the selected maternal and fetal nucleic acid regions from the first and second chromosomes and allele of interest which were amplified with the universal primers by counting each nucleic acid region an average of at least 100 times in a single sequencing run, wherein detecting the amplified selected maternal and fetal nucleic acid sequences from the first and second chromosomes is not reliant on detection of any polymorphism within the selected nucleic acid regions from the first and second chromosomes;

(f) quantifying a combined relative frequency of the amplified selected maternal and fetal nucleic acid regions from the first and second chromosomes of interest;

(g) comparing the combined relative frequencies of the amplified selected maternal and fetal nucleic acid regions from the first and second chromosomes of interest;

(h) identifying the presence or absence of a statistical variation in the compared combined relative frequencies of the amplified selected maternal and fetal nucleic acid regions of the first chromosome and the combined relative frequencies of the amplified selected maternal and fetal nucleic acid regions of the second chromosome indicative of the presence or absence of a fetal aneuploidy, and identifying the presence of a fetal aneuploidy when the statistical variation is present and identifying the absence of a fetal aneuploidy when a statistical variation is absent;

(i) determining if the amplified selected maternal and fetal nucleic acid regions from the allele of interest are detected in a frequency indicative of fetal inheritance of the allele.

19. The method of claim 18, wherein the combined relative frequencies of the amplified selected maternal and fetal nucleic acid regions from each of the first and second chromosomes and the allele of interest are individually quantified, and the combined relative frequencies of the individual amplified selected maternal and fetal nucleic acid regions from the first and second chromosomes are compared.

20. The method of claim 18, wherein the amplified selected maternal and fetal nucleic acid regions from the first and second chromosomes and allele of interest are normalized following detection and prior to quantification.

21. The method of claim 18, wherein the amplified selected maternal and fetal nucleic acid regions from the first and second chromosomes and allele of interest are associated with one or more identifying indices.

22. The method of claim 21, wherein the combined relative frequencies of the amplified selected maternal and fetal nucleic acid regions from the first and second chromosomes and allele of interest are determined through identification of the associated one or more identifying indices.

23. The method of claim 18, wherein the amplified selected maternal and fetal nucleic acid regions from the first and second chromosomes and allele of interest are quantified by counting each nucleic acid region an average of at least 500 times.

24. The method of claim 1, wherein the method is performed with maternal plasma.

25. The method of claim 18, wherein the allele of interest is putatively associated with a Robertsonian translocation.

26. The method of claim 18, wherein the locus is putatively associated with a Robertsonian translocation.

27. The method of claim 18, wherein the allele of interest is putatively associated with a Robertsonian translocation.

28. The method of claim 18, wherein the number of amplification cycle using the universal primers is 20 cycles or more.

29. The method of claim 18, wherein the number of amplification cycle using the primers complementary to the selected nucleic acid regions is 5-30.

* * * * *